United States Patent
Heil et al.

(10) Patent No.: US 8,795,847 B2
(45) Date of Patent: Aug. 5, 2014

(54) MATERIALS FOR ORGANIC ELECTROLUMINESCENT DEVICES

(75) Inventors: Holger Heil, Darmstadt (DE); Philipp Stoessel, Frankfurt am Main (DE); Amir Parham, Frankfurt (DE); Horst Vestweber, Gilserberg-Wintercheid (DE)

(73) Assignee: Merck Patent GmbH (DE)

( * ) Notice: Subject to any disclaimer, the term of this patent is extended or adjusted under 35 U.S.C. 154(b) by 1239 days.

(21) Appl. No.: 12/096,464

(22) PCT Filed: Nov. 17, 2006

(86) PCT No.: PCT/EP2006/011029
§ 371 (c)(1),
(2), (4) Date: Jun. 6, 2008

(87) PCT Pub. No.: WO2007/065550
PCT Pub. Date: Jun. 14, 2007

(65) Prior Publication Data
US 2008/0303003 A1    Dec. 11, 2008

(30) Foreign Application Priority Data

Dec. 8, 2005    (DE) .......................... 10 2005 058 557
Mar. 2, 2006    (DE) .......................... 10 2006 009 630

(51) Int. Cl.
*H01L 51/54*    (2006.01)

(52) U.S. Cl.
USPC ........... 428/690; 428/917; 313/504; 313/505; 313/506; 257/40; 257/E51.05; 257/E51.026; 257/E51.032; 585/27

(58) Field of Classification Search
USPC .................. 428/690, 917; 313/504, 505, 506; 257/40, E51.05, E51.032, E51.026; 585/27
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,840,217 A | 11/1998 | Lupo et al. | |
| 5,935,721 A | 8/1999 | Shi et al. | |
| 6,458,909 B1 | 10/2002 | Spreitzer et al. | |
| 6,506,504 B1 | 1/2003 | Kwon et al. | |
| 6,534,199 B1 | 3/2003 | Hosokawa et al. | |
| 6,713,192 B2 | 3/2004 | Fukuoka et al. | |
| 2005/0064233 A1 | 3/2005 | Matsuura et al. | |
| 2005/0089717 A1* | 4/2005 | Cosimbescu et al. | 428/690 |
| 2005/0095455 A1 | 5/2005 | Nomura et al. | |
| 2005/0214565 A1 | 9/2005 | Ikeda et al. | |
| 2005/0233165 A1 | 10/2005 | Ido et al. | |
| 2006/0033421 A1 | 2/2006 | Matsuura et al. | |
| 2006/0043858 A1 | 3/2006 | Ikeda et al. | |
| 2006/0127698 A1* | 6/2006 | Tokailin et al. | 428/690 |
| 2006/0134456 A1 | 6/2006 | Ikeda et al. | |
| 2006/0175958 A1 | 8/2006 | Gerhard et al. | |
| 2006/0226768 A1 | 10/2006 | Yu et al. | |
| 2007/0164273 A1 | 7/2007 | Gerhard et al. | |
| 2007/0170419 A1 | 7/2007 | Gerhard et al. | |

FOREIGN PATENT DOCUMENTS

| | | |
|---|---|---|
| CN | 1362464 | 8/2002 |
| EP | 0676461 A2 | 10/1995 |
| EP | 0681019 A2 | 11/1995 |
| EP | 1167488 A1 | 1/2002 |
| EP | 1533289 A1 | 5/2005 |
| EP | 1533290 A1 | 5/2005 |
| EP | 1553154 A1 | 7/2005 |
| JP | 2004103463 | 4/2004 |
| WO | WO-98/27136 A1 | 6/1998 |
| WO | WO-01/21729 A1 | 3/2001 |
| WO | WO-01/76323 A1 | 10/2001 |
| WO | WO-03/087023 A1 | 10/2003 |
| WO | WO-03/095445 A1 | 11/2003 |
| WO | WO-2004/013073 A1 | 2/2004 |
| WO | WO-2004/016575 A1 | 2/2004 |
| WO | WO-2004/018587 A1 | 3/2004 |
| WO | WO-2004/018588 A1 | 3/2004 |
| WO | WO-2005/011013 A1 | 2/2005 |
| WO | WO-2005/084081 A1 | 9/2005 |
| WO | WO-2005/084082 A1 | 9/2005 |
| WO | WO-2006/000388 A1 | 1/2006 |
| WO | WO-2006/000389 A1 | 1/2006 |
| WO | WO-2006/058737 A1 | 6/2006 |

OTHER PUBLICATIONS

Matsumoto et al, Synthesis and Electronic Properties of 9,10-Disilylanthracenes, 1996, Organometallics, vol. 15, pp. 1067-1070.*

* cited by examiner

*Primary Examiner* — Gregory Clark
(74) *Attorney, Agent, or Firm* — Drinker Biddle & Reath LLP

(57) ABSTRACT

The present invention relates to anthracene derivatives, to the use thereof in organic electroluminescent devices, and to organic electroluminescent devices comprising these compounds.

20 Claims, No Drawings

MATERIALS FOR ORGANIC ELECTROLUMINESCENT DEVICES

RELATED APPLICATIONS

This application is a national stage application (under 35 U.S.C. §371) of PCT/EP2006/011029, filed Nov. 17, 2006, which claims benefit of German application 10 2005 058 557.4, filed Dec. 8, 2005, and German application 10 2006 009 630.4, filed Mar. 2, 2006.

The present invention describes novel anthracene derivatives, the use of these compounds in organic electroluminescent devices, and organic electroluminescent devices comprising these compounds.

Organic semiconductors are used as functional materials in a number of applications of different types which can be ascribed to the electronics industry in the broadest sense. The general structure of organic electroluminescent devices which are capable of the emission of light in the visible spectral region is described, for example, in U.S. Pat. No. 4,539,507, U.S. Pat. No. 5,151,629, EP 0676461 and WO 98/27136.

However, these devices still have considerable problems which require urgent improvement for use in high-quality full-colour displays:

1. The compounds used do not have adequate thermal stability and do not have a sufficiently high glass-transition temperature.
2. The compounds used are not sufficiently soluble in organic solvents, which makes their purification during preparation and cleaning of the vapour-deposition units (for example the shadow masks) more difficult.
3. The hole and electron stability (redox stability) of the compounds used to date is still inadequate.

The closest prior art which may be mentioned is the use of various condensed aromatic compounds, in particular anthracene or pyrene derivatives, as host materials, in particular for blue-emitting electroluminescent devices. The host material known in accordance with the prior art is 9,10-bis(2-naphthyl)anthracene (U.S. Pat. No. 5,935,721). Further anthracene derivatives which are suitable as host materials are described, for example, in WO 01/076323, in WO 01/021729, in WO 04/013073, in WO 04/018588, in WO 03/087023 or in WO 04/018587. Host materials based on aryl-substituted pyrenes and chrysenes are described in WO 04/016575, which in principle also encompasses corresponding anthracene and phenanthrene derivatives. WO 03/095445 and CN 1362464 describe 9,10-bis(1-naphthyl)anthracene derivatives for use in OLEDs.

The object of the present invention was to provide compounds having improved properties, in particular improved host materials and improved blue and green emitters.

Surprisingly, it has been found that organic electroluminescent devices which comprise certain anthracene derivatives which are substituted by trialkylsilyl groups have significant improvements over the prior art. These compounds have high thermal stability, a high glass-transition temperature, high redox stability and good solubility in organic solvents. The present invention therefore relates to these compounds and to the use thereof in OLEDs.

The invention relates to silyl-substituted compounds of the formula (1)

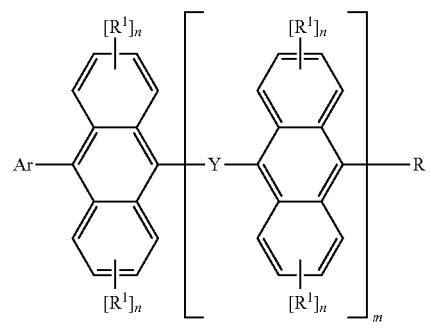

Formula (1)

where the following applies to the symbols and indices used:

Ar is a 1-naphthyl group or a 9-anthryl group, in which one or two carbon atoms may be replaced by N and which may be substituted by one or more radicals $R^1$ and/or which may be substituted by one or more radicals $N(Ar^1)_2$, where the two radicals $Ar^1$ may also be connected to one another by a single bond or an O, S, $N(R^1)$ or $C(R^1)_2$ group;

R is an aromatic or heteroaromatic ring system having 5 to 40 aromatic ring atoms, which may be substituted by one or more radicals $R^1$, or an $N(Ar^1)_2$ group, where the two radicals $Ar^1$ may also be connected to one another by a single bond or an O, S, $N(R^1)$ or $C(R^1)_2$ group;

$Ar^1$ is on each occurrence, identically or differently, an aromatic or heteroaromatic ring system having 5 to 40 aromatic ring atoms, which may be substituted by one or more radicals $R^1$;

Y is on each occurrence, identically or differently, a divalent group containing 1 to 40 C atoms or —O—, —S—, —$NR^1$—, —P(=O)$R^1$— or a single bond;

$R^1$ is, identically or differently on each occurrence, $Si(R^2)_3$, F, Cl, Br, I, CN, $N(R^3)_2$, $NO_2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^3$, where one or more non-adjacent $CH_2$ groups may be replaced by —$R^3C=CR^3$—, —C≡C—, $Si(R^3)_2$, $Ge(R^3)_2$, $Sn(R^3)_2$, C=O, C=S, C=Se, C=$NR^3$, —O—, —S—, —N($R^3$)— or —CON$R^3$— and where one or more H atoms may be replaced by F, Cl, Br, I, CN or $NO_2$, or an aryl or heteroaryl group having 5 to 24 aromatic ring atoms, which may be substituted by one or more radicals $R^3$, or an aryloxy or heteroaryloxy group having 5 to 24 aromatic ring atoms, which may be substituted by one or more radicals $R^3$, or a combination of two, three, four or five of these systems; two or more adjacent substituents $R^1$ here may also form a mono- or polycyclic, aliphatic ring system with one another;

$R^2$ is on each occurrence, identically or differently, a straight-chain alkyl group having 1 to 40 C atoms or a branched or cyclic alkyl group having 3 to 40 C atoms, in each of which one or more non-adjacent $CH_2$ groups which are not bonded directly to the silicon may be replaced by —$R^3C=CR^3$—, —C≡C—, $Si(R^3)_2$, $Ge(R^3)_2$, $Sn(R^3)_2$, C=O, C=S, C=Se, C=$NR^3$, —O—, —S—, —N($R^3$)— or —CON$R^3$— and in each of which one or more H atoms may be replaced by F, Cl, Br, I, CN or $NO_{21}$ and which may also be substituted by an aryl or heteroaryl group having 5 to 24 aromatic ring atoms, which may be substituted by one or more radicals $R^3$, or by an aryloxy or heteroaryloxy group having 5 to 24 aromatic ring atoms, which may be substituted by one or more radicals $R^3$; two or more substituents $R^2$ here may also form a mono- or polycyclic ring system with one another;

$R^3$ is on each occurrence, identically or differently, H or a hydrocarbon radical having 1 to 20 C atoms, which may be aliphatic or aromatic or a combination of aliphatic and aromatic and which may also be substituted by F; two or more radicals $R^3$ here may also form a mono- or polycyclic, aliphatic or aromatic ring system with one another;

n is, identically or differently on each occurrence, 0, 1, 2, 3 or 4;

m is 0, 1, 2, 3, 4 or 5;

characterised in that at least one radical $R^1$ which represents an $Si(R^2)_3$ group is present in the molecule.

For the purposes of this invention, an aryl group or a heteroaryl group is taken to mean an aromatic group or heteroaromatic group respectively having a common aromatic π-electron system. For the purposes of this invention, this may be a simple homo- or heterocycle, for example benzene, pyridine, thiophene, etc., or it may be a condensed aryl or heteroaryl group in which at least two aromatic or heteroaromatic rings, for example benzene rings, are "fused" to one another, i.e. are condensed onto one another by anellation, i.e. have at least one common edge and thus also a common aromatic π-electron system. These aryl or heteroaryl groups may be substituted or unsubstituted; any substituents present may likewise form further ring systems. Thus, for example, systems such as naphthalene, anthracene, phenanthrene, pyrene, etc., are regarded as aryl groups and quinoline, acridine, benzothiophene, carbazole, etc., are regarded as heteroaryl groups for the purposes of this invention, while, for example, biphenyl, fluorene, spirobifluorene, etc., do not represent aryl groups since they involve separate aromatic electron systems.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (less than 10% of the atoms other than H, preferably less than 5% of the atoms other than H), such as, for example, an sp3-hybridised C, N or O atom. Thus, for example, systems such as 9,9'-spirobifluorene, fluorene, 9,9-diarylfluorene, triarylamine, diaryl ether, etc., are also intended to be taken to mean aromatic ring systems for the purposes of this invention. Part of the aromatic or heteroaromatic ring system may also be a condensed group here.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. An aromatic or heteroaromatic ring system having 1 to 30 aromatic ring atoms, which may also in each case be substituted by the above-mentioned radicals $R^1$ or $R^2$ and which may be linked to the aromatic or heteroaromatic ring system via any desired positions, is taken to mean, in particular, groups derived from benzene, naphthalene, anthracene, phenanthrene, pyrene, chrysene, perylene, fluoranthene, tetracene, pentacene, benzopyrene, biphenyl, biphenylene, terphenyl, terphenylene, fluorene, spirobifluorene, truxene, isotruxene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzo pyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pterldine, indolizine and benzothiadiazole.

Preference is given to compounds of the formula (1) in which the symbol Ar stands for a 1-naphthyl group, a 9-anthryl group, a 1-, 4-, 5- or 8-isoquinolinyl group or a 4- or 5-quinolinyl group. Particular preference is given to compounds of the formula (1) in which the symbol Ar stands for a 1-naphthyl group or a 9-anthryl group. Very particular preference is given to the compounds of the formulae (1a) to (1d)

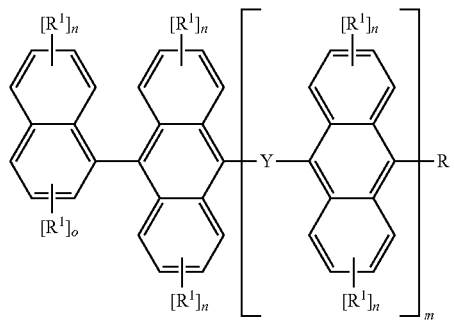

Formula (1a)

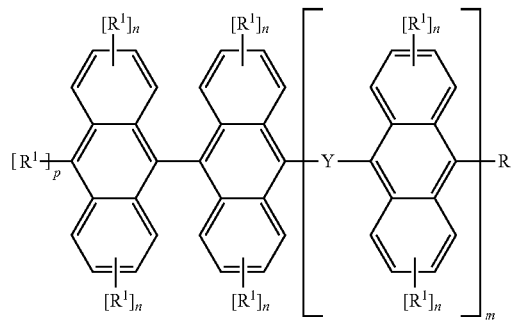

Formula (1b)

-continued

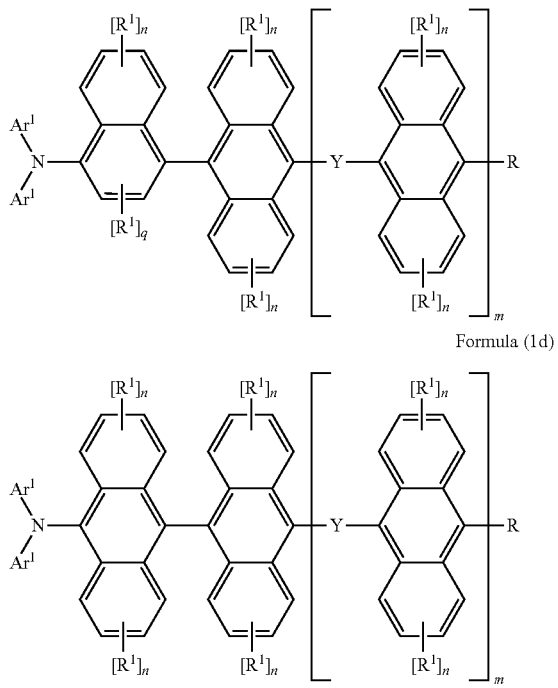

Formula (1c)

Formula (1d)

where R¹, Ar¹, R¹, Y, m and n have the meaning defined above, where the two radicals Ar¹ may also be connected to one another by a single bond or an O, S, N(R¹) or C(R¹)$_2$ group, and furthermore the following applies:

o is 0, 1, 2 or 3;

p is 0 or 1;

q is 0, 1 or 2;

characterised in that at least one radical R¹ which stands for an Si(R²)$_3$ group is present.

In compounds of the formula (1b), the index p is preferably 1, i.e. a further substituent other than hydrogen is preferably bonded to the anthryl group in the 10-position.

Preference is furthermore given to compounds of the formulae (1) and (1a) to (1d) in which the symbol R stands for an aromatic or heteroaromatic ring system having 6 to 24 aromatic ring atoms, which may be substituted by one or more radicals R¹, or in which the symbol R stands for a group of the formula (2a) or (2b)

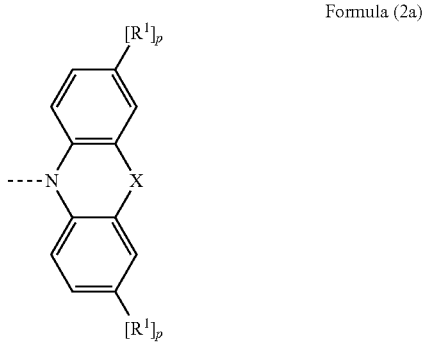

Formula (2a)

Formula (2b)

where R¹ and p have the meaning indicated above, and furthermore the following applies:

X stands for a single bond, O, S, N(R¹) or C(R¹)$_2$;

Ar¹ is, identically or differently on each occurrence, an aryl or heteroaryl group having 5 to 20 aromatic ring atoms, which may be substituted by one or more radicals R¹, preferably an aryl or heteroaryl group having 6 to 14 aromatic ring atoms, which may be substituted by one or more radicals R¹, particularly preferably phenyl, 1-naphthyl or 2-naphthyl, each of which may be substituted by one or more radicals R¹.

If a substituent on the Ar group stands for an N(Ar¹)$_2$ group, this substituent is also preferably selected from the formulae (2a) and (2b) indicated above.

If the symbol R stands for an aromatic or heteroaromatic ring system, it preferably stands for an aromatic or heteroaromatic ring system having 9 to 24 aromatic ring atoms, which may be substituted by one or more radicals R¹. Particular preference is given to compounds of the formula (1) in which the symbol R stands for a condensed aryl or heteroaryl group having 10 to 16 aromatic ring atoms or for an aromatic, optionally bridged biaryl group, each of which may be substituted by one or more radicals R¹. Very particular preference is given to compounds of the formula (1) in which the symbol R, if it stands for an aromatic or heteroaromatic ring system, stands, identically or differently on each occurrence, for a 1-naphthyl, 2-naphthyl, 9-anthryl, 2-phenanthrenyl, 9-phenanthrenyl, quinolinyl, isoquinolinyl, ortho-, meta- or para-biphenyl, 2-fluorenyl or 2-spirobifluorenyl group, each of which may be substituted by one or more radicals R¹, in particular for 1-naphthyl, which may be substituted by one or more radicals R¹.

Preference is furthermore given to compounds of the formulae (1) and (1a) to (1d) which, if the group R stands for an aromatic or heteroaromatic ring system, have hindered rotation about the anthracene-R bond. For the purposes of this invention, hindered rotation is taken to mean a rotation barrier of at least 80 kJ/mol, preferably at least 100 kJ/mol, particularly preferably at least 120 kJ/mol, at room temperature. This rotation barrier can be determined experimentally by temperature-dependent NMR measurements. If the compound of the formula (1) or (1a) or (1b) exhibits atropisomerism about one or more bonds, the invention in each case also relates to OLEDs comprising the corresponding isolated or enriched atropisomers. This relates both to enantiomers and also to diastereomers. Hindered rotation about the anthracene-R bond is achieved if the group R has at least one organic substituent in the ortho-position and/or if the group R is, for example, a 1-naphthyl group which contains peri-hydrogen atoms.

Both compounds of the formula (1) in which the two groups Ar and R are selected identically and also compounds of the formula (1) in which the groups Ar and R are different are in accordance with the invention.

Preference is furthermore given to compounds of the formulae (1) and (1a) to (1d) in which the symbol R¹, identically or differently on each occurrence, stands for Si(R²)$_3$, F, a straight-chain alkyl or alkoxy group having 1 to 6 C atoms or a branched or cyclic alkyl or alkoxy group having 3 to 10 C atoms, in each of which one or more CH$_2$ groups may be replaced by —R$^3$C═CR$^3$—, Si(R$^3$)$_2$, —O—, —S— or —N(R$^3$)— and in each of which one or more H atoms may be replaced by F, or an aryl or heteroaryl group having 5 to 14 aromatic ring atoms, which may be substituted by one or more radicals R$^3$, or a combination of two or three of these systems; two or more radicals R$^1$ here may also form a mono- or polycyclic, aliphatic ring system with one another. Particularly preferred radicals R$^1$ are selected from the group consisting of Si(R$^2$)$_3$, F, straight-chain alkyl groups having 1 to 4 C atoms and branched alkyl groups having 3 to 5 C atoms, in each of which one or more H atoms may be replaced by F, or aryl or heteroaryl groups having 6 to 10 aromatic ring atoms, or a combination of two of these systems; two or more adjacent radicals R$^1$ here may also form a mono- or polycyclic, aliphatic ring system with one another.

Preference is furthermore given to compounds of the formulae (1) and (1a) to (1d) in which the symbol Y, identically or differently on each occurrence, represents a linear alkylene group having 1 to 10 C atoms or a branched or cyclic alkylene or alkylidene group having 3 to 10 C atoms, a divalent aromatic group having 6 to 25 C atoms, C═O, —O—, —S— or a group of the formula —N(R$^1$)— or —P(═O)R$^1$— or a single bond. Particular preference is given to compounds in which the symbol Y, identically or differently on each occurrence, represents a linear alkylene group having 1 to 4 C atoms, a branched alkylene or alkylidene group having 3 to 5 C atoms, a cyclic alkylene group having 3 to 10 C atoms, a divalent aromatic group selected from groups derived from benzene, naphthalene, biphenyl or terphenyl, or C═O, —N(R$^3$)— or —P(═O)R$^3$— or a single bond.

Preference is furthermore given to compounds of the formulae (1) and (1a) to (1d) in which the index m stands for 0, 1 or 2, particularly preferably 0 or 1.

Preference is furthermore given to compounds of the formulae (1) and (1a) to (1d) in which the index n stands for 0, 1 or 2, particularly preferably 0 or 1, where at least one radical R$^1$ which stands for Si(R$^2$)$_3$ is present in the molecule. The compound of the formulae (1) and (1a) to (1d) preferably contains one, two, three or four groups of the formula Si(R$^2$)$_3$, particularly preferably one or two groups of the formula Si(R$^2$)$_3$.

The groups of the formula Si(R$^2$)$_3$ can be bonded in various positions of the molecule. In a preferred embodiment of the invention, at least one group of the formula Si(R$^2$)$_3$ is bonded to the central anthracene unit, preferably in the 2-position and/or in the 6-position of the anthracene. In a further preferred embodiment of the invention, at least one group of the formula Si(R$^2$)$_3$ is bonded to the group Ar. If the group Ar represents a 1-naphthyl group, the group of the formula Si(R$^2$)$_3$ is preferably bonded in the 4-position of the naphthyl group. If the group Ar represents a 9-anthryl group, the group of the formula Si(R$^2$)$_3$ is preferably bonded in the 10-position of the anthracene group or in the 2-position or 2,6-position if another radical R$^1$ is bonded in the 10-position. In still a further preferred embodiment of the invention, at least one group of the formula Si(R$^2$)$_3$ is bonded to the group R. If the group R represents an aryl group or a heteroaryl group, the group of the formula Si(R$^2$)$_3$ is preferably bonded in the para-position to the aryl group. If the group R represents a group of the formula N(Ar$^1$)$_2$, the group of the formula Si(R$^2$)$_3$ is preferably bonded to one or both groups Ar$^1$ in the para-position to the nitrogen.

Preferred radicals R$^2$ on the silyl group are selected from straight-chain alkyl groups having 1 to 10 C atoms and branched or cyclic alkyl groups having 3 to 10 C atoms, in each of which one or more non-adjacent CH$_2$ groups which are not bonded directly to the silicon may be replaced by 0 and in each of which one or more H atoms may be replaced by F; two or more substituents R$^2$ here may also form a mono- or polycyclic ring system with one another. Particularly preferred radicals R$^2$ on the silyl group are selected from straight-chain alkyl groups having 1 to 4 C atoms or branched alkyl groups having 3 or 4 C atoms, in each of which one or more H atoms may be replaced by F. Very particularly preferred groups R$^2$ are methyl, CF$_3$, ethyl, isopropyl and tert-butyl. Very particularly preferred Si(R$^2$)$_3$ groups are Si(Me)$_3$, Si(Me)$_2$(t-Bu), SiMe(t-Bu)$_2$ and Si(i-Pr)$_3$.

Preference is furthermore given to compounds of the formula (1) whose molecular weight is between 400 and 1500 g/mol, particularly preferably between 400 and 900 g/mol.

Various processes are available for the preparation of the compounds according to the invention. If the silyl group is to be introduced on the anthracene, a suitable starting compound is 2-bromoanthraquinone or 2,6-dibromoanthraquinone or the corresponding chloroanthraquinone derivative. This can in each case be reacted with a reactive organometallic reagent, for example an aryl-Grignard reagent or aryllithium reagent, and reduced in a subsequent step, for example using tin(II) chloride, giving 9,10-diarylanthracene derivatives which also carry bromine or chlorine in the 2- or 2,6-position. Metallation, for example lithiation, and reaction with a silyl halide, for example trialkylsilyl chloride, results in the corresponding silylated target compound.

If the silyl group is not to be introduced onto the central anthracene, but instead onto the aromatic Ar or R groups, it is also possible to introduce it in a first step and only then to couple the aromatic group to the anthracene in a further step. Thus, a dibromoaromatic compound can be selectively monolithiated and reacted with a silyl halide to give a bromosilylaromatic compound. This can in turn be converted by lithiation into the corresponding boronic acid or a boronic acid derivative, which can then be coupled to dibromoanthracene or another anthracene derivative in a Suzuki coupling with palladium catalysis. Further coupling reactions between the aromatic compound and the anthracene are suitable analogously, for example the Stille coupling. If the R group represents a diarylamino group, a Hartwig-Buchwald coupling is suitable.

This invention furthermore relates to a process for the preparation of the compounds of the formula (1) according to the invention which carry one or more Si(R$^2$)$_3$ groups on the Ar or R group, by coupling a functionalised Ar or R group which is substituted by one or more Si(R$^2$)$_3$ groups to a corresponding anthracene derivative. The coupling is preferably a transition metal-catalysed coupling reaction, in particular a Suzuki coupling, a Stille coupling or a Hartwig-Buchwald coupling. The functionalisation of the Ar or R group here may be a boronic acid derivative for use in a Suzuki coupling. The group may be a trialkyltin derivative for use in a Stille coupling. It may be an N—H functionality for use in a Hartwig-Buchwald coupling. It may furthermore be a brominated compound if the anthracene is correspondingly substituted by a boronic acid derivative or by a trialkyltin derivative. It is surprising here that the silyl group on the Ar or R group can be employed with no damage in the metal-catalysed coupling reaction and that this does not result in side reactions.

Examples of preferred compounds of the formula (1) are compounds (A1) to (A68) depicted below.

(A1) 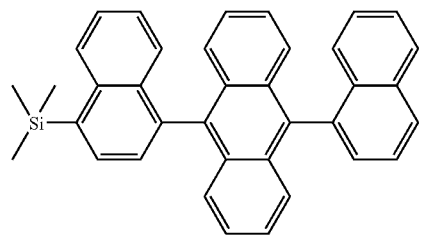
(A2) 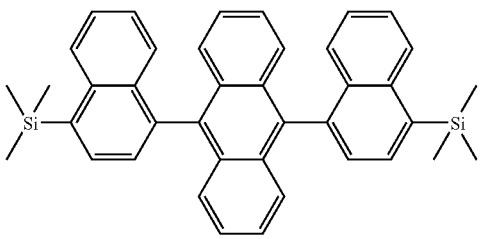
(A3) 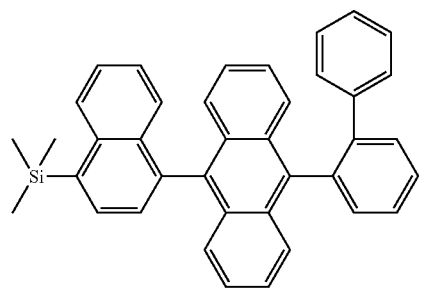
(A4) 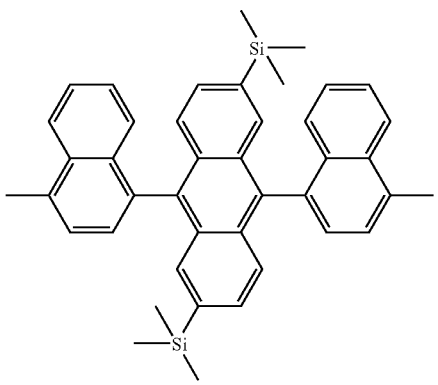
(A5) 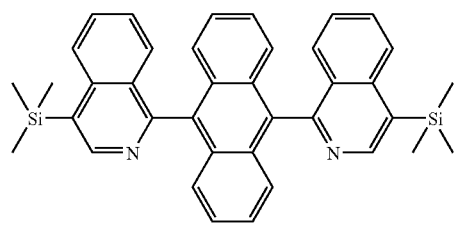
(A6) 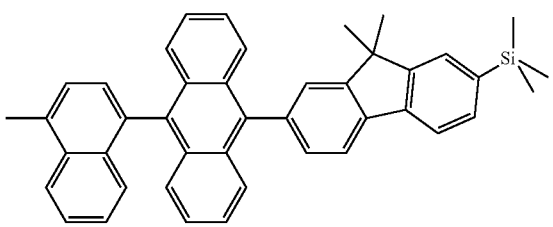
(A7) 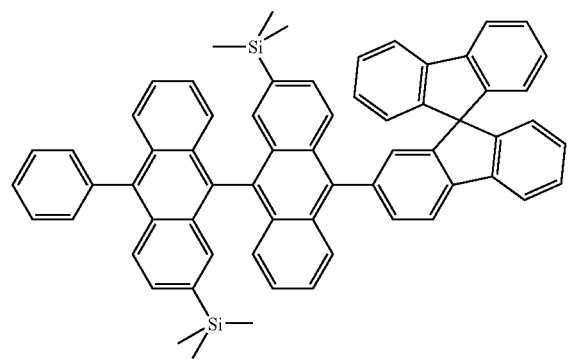
(A8) 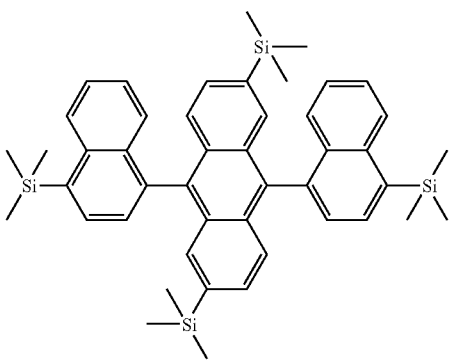
(A9) 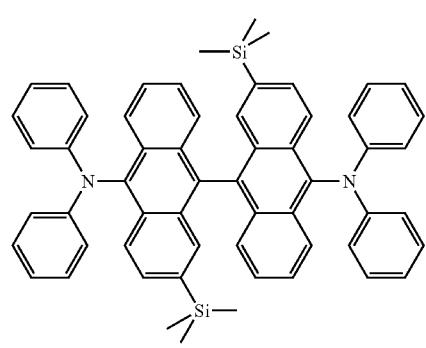
(A10) 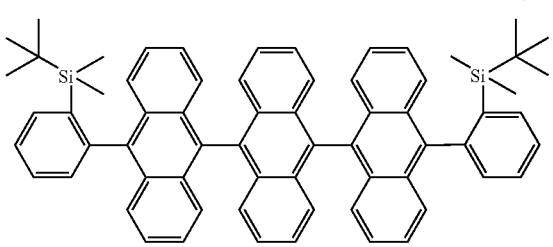

-continued
(A11)
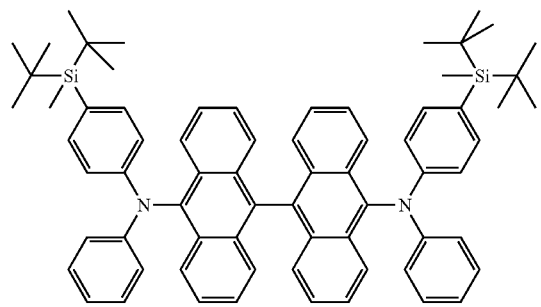
(A12)
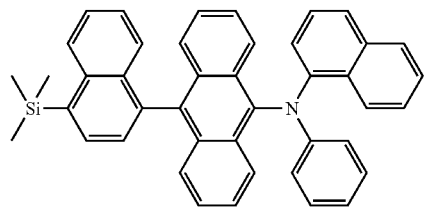
(A13)
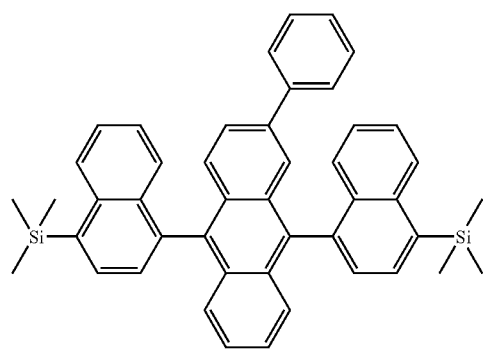
(A14)
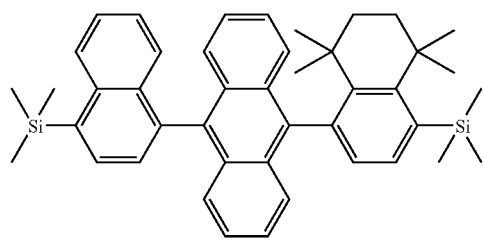
(A15)
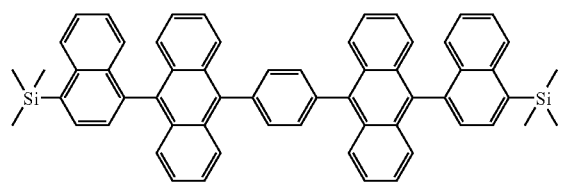
(A16)
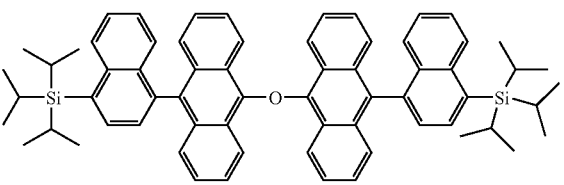
(A17)
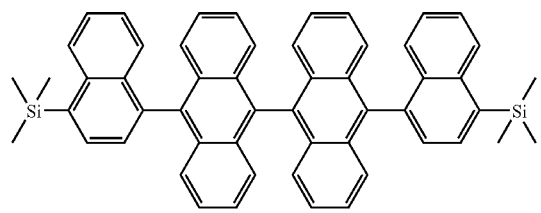
(A18)
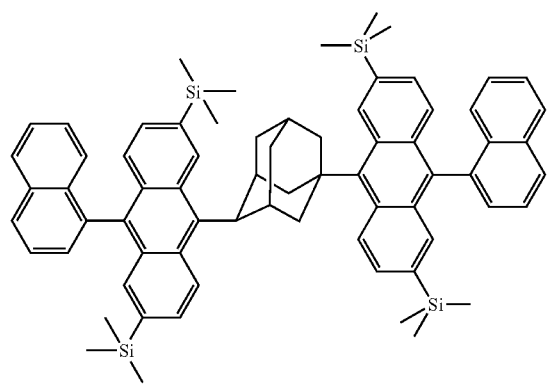

(A19)
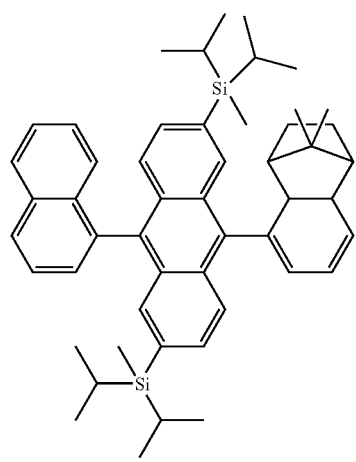
(A20)
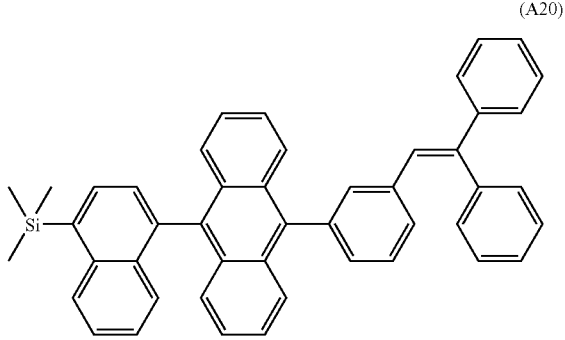
(A21)
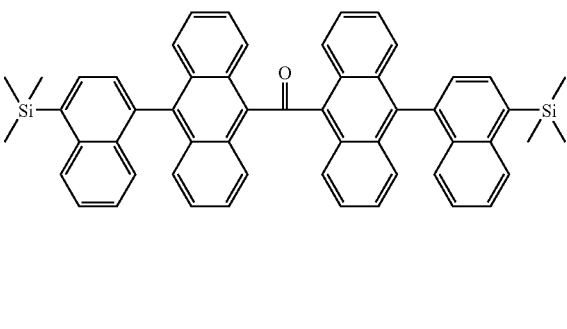
(A22)
(A23)
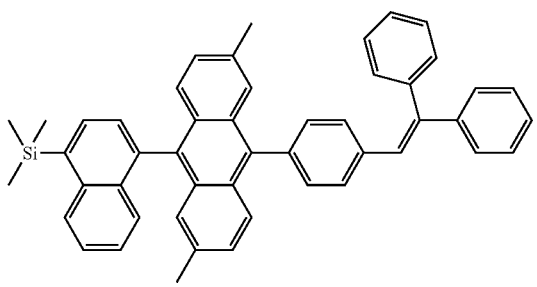
(A24)
(A25)
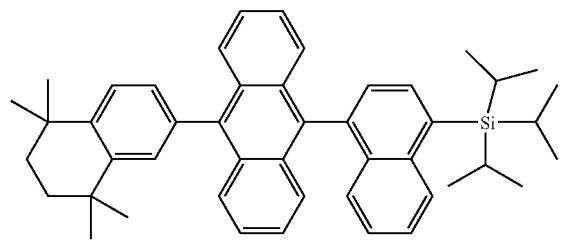
(A26)
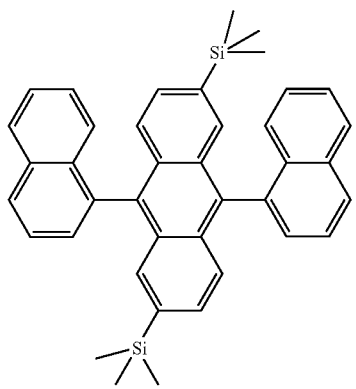

-continued
(A27)
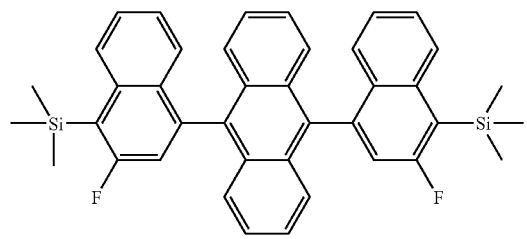
(A28)
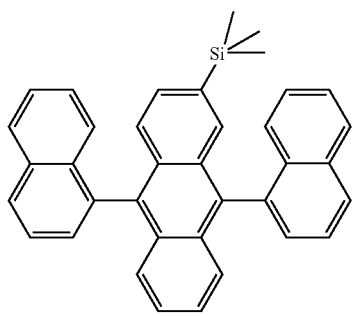
(A29)
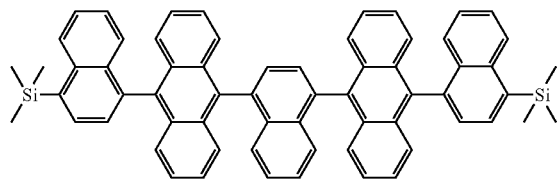
(A30)
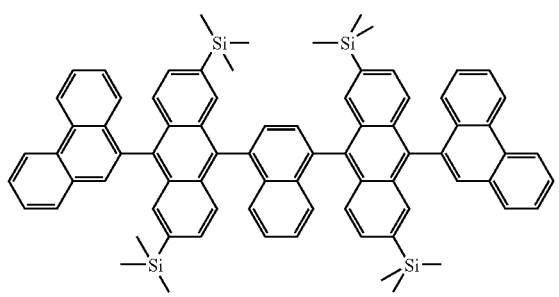
(A31)
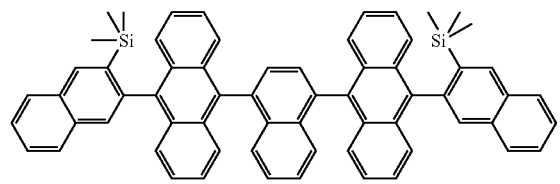
(A32)
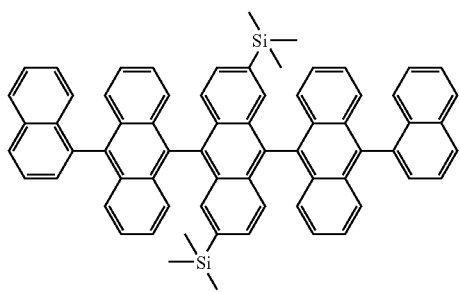
(A33)
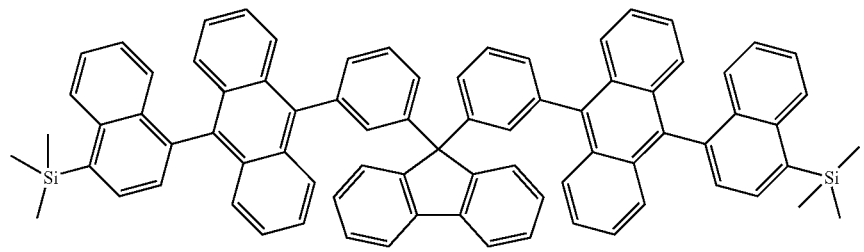
(A34)
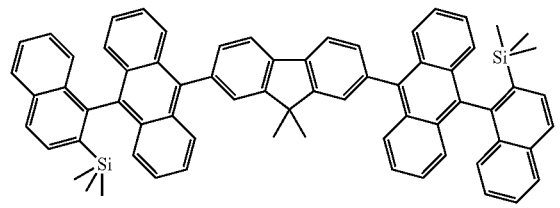
(A35)
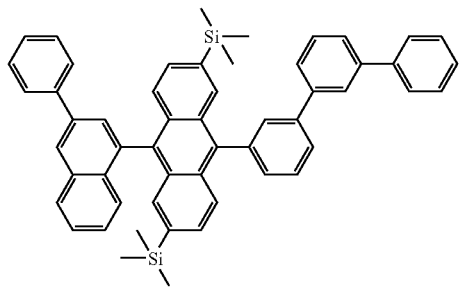

-continued
(A36)
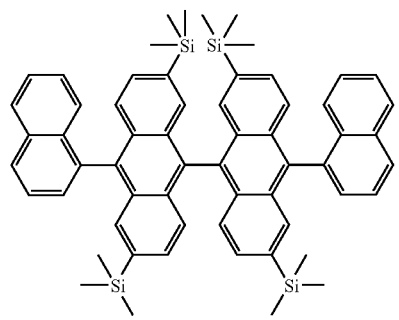
(A37)
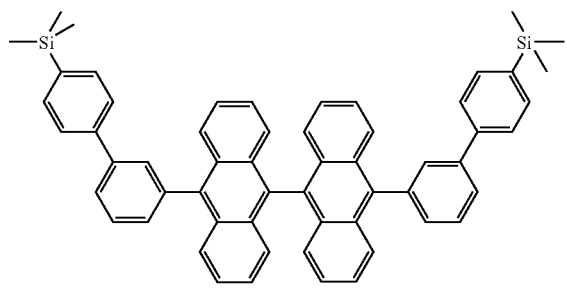
(A38)
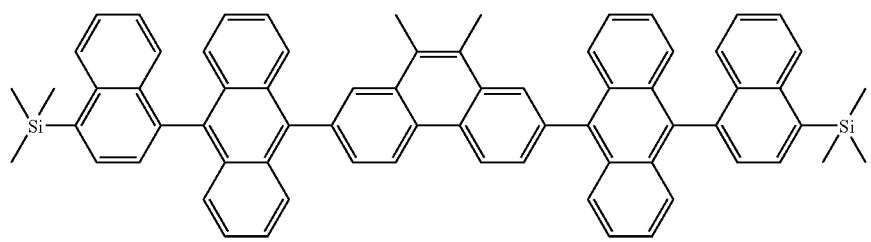
(A39)
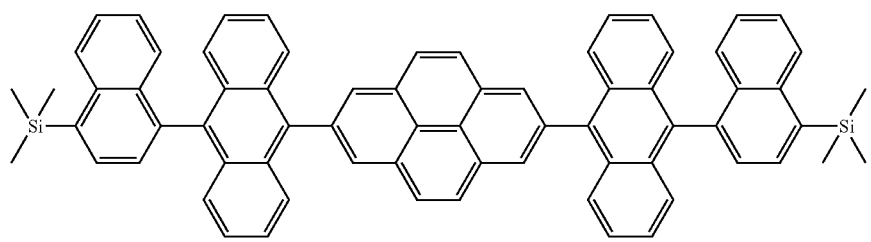
(A40)
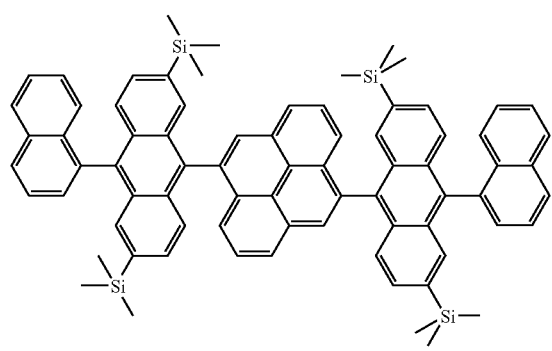
(A41)
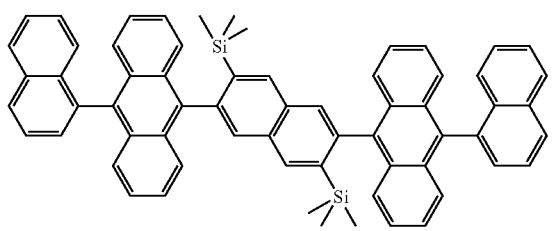
(A42)
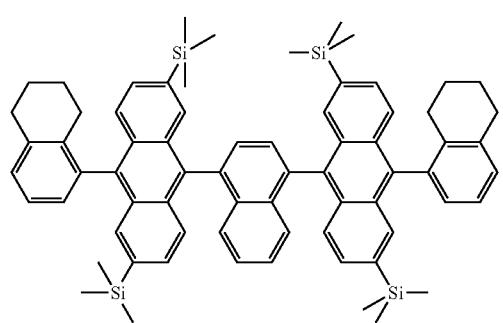

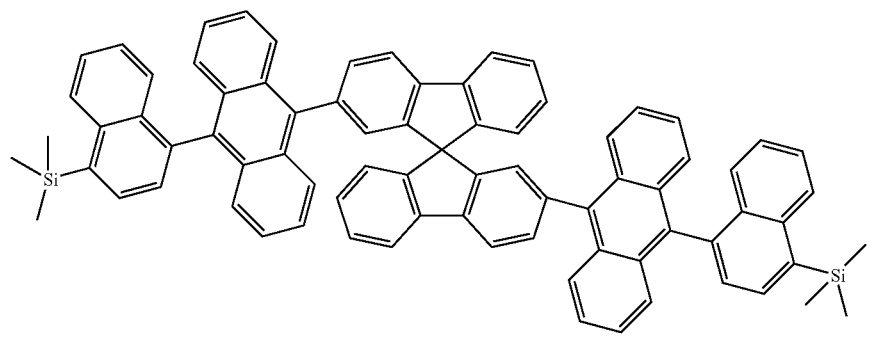
(A43)
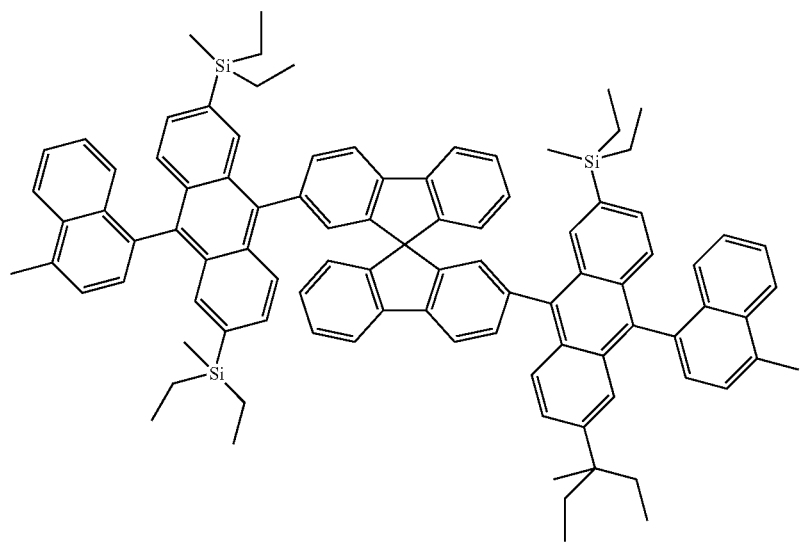
(A44)
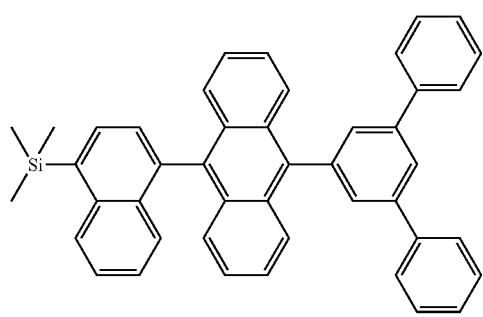
(A45)
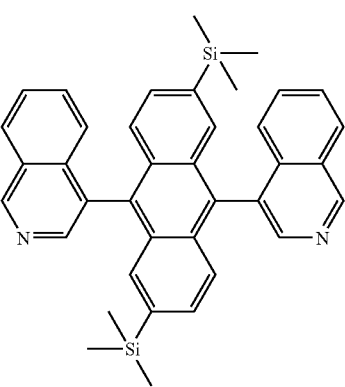
(A46)

-continued
(A47)
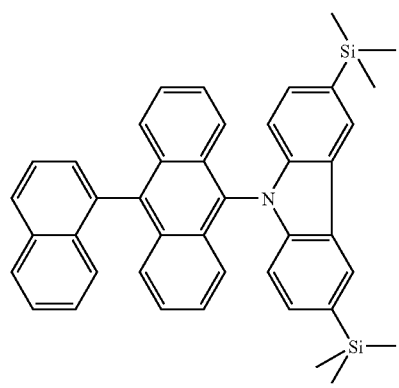
(A48)
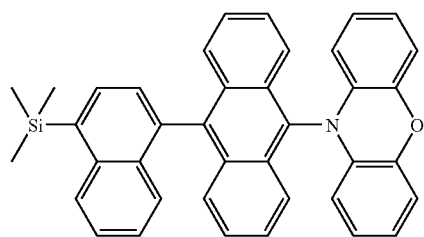
(A49)
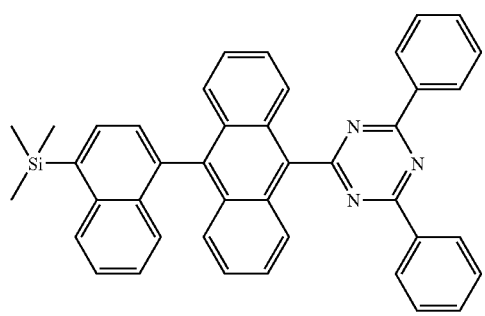
(A50)
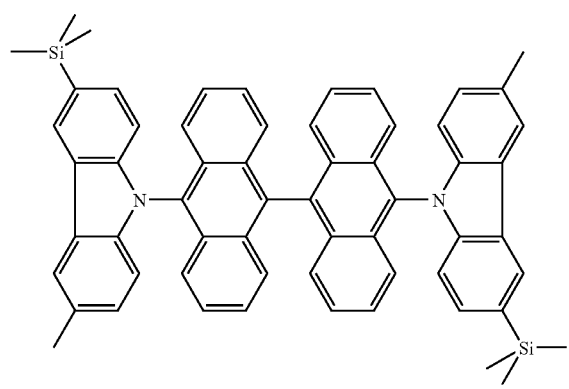
(A51)
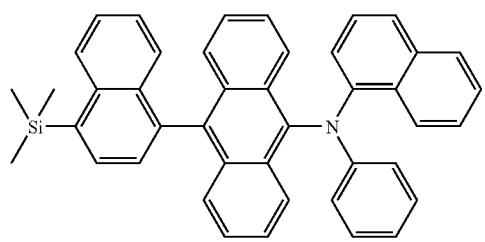
(A52)
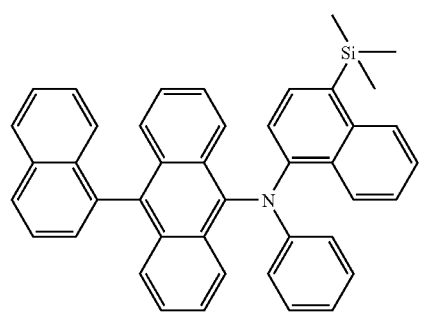
(A53)
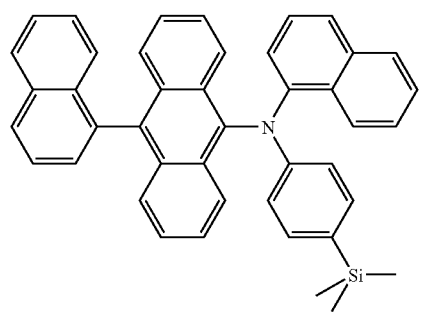
(A54)
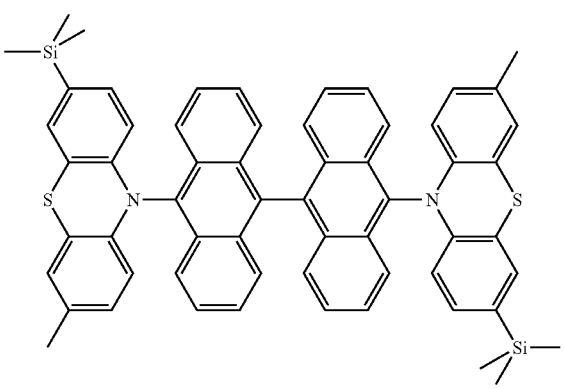

-continued
(A55)
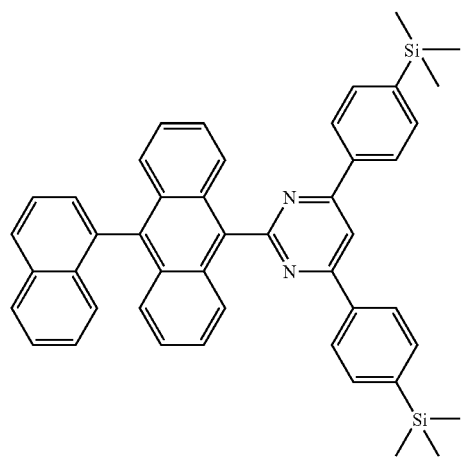
(A56)
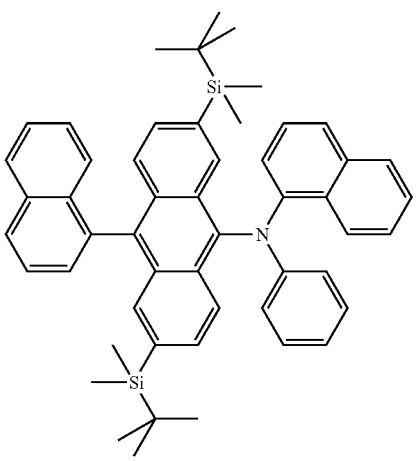
(A57)
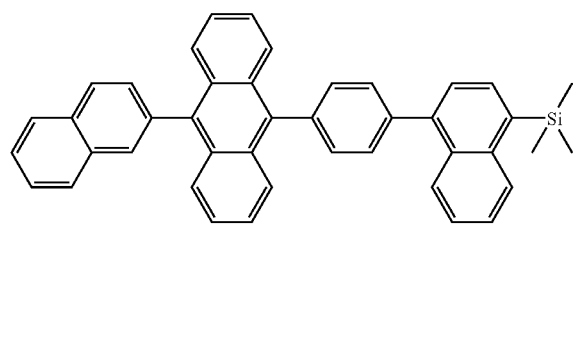
(A58)
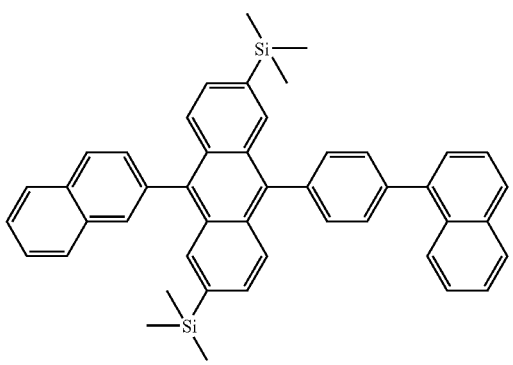
(A59)
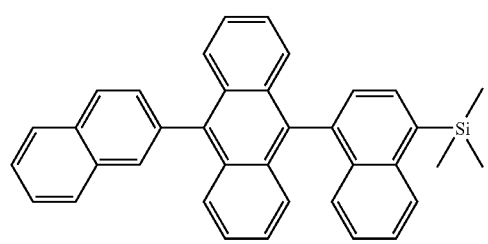
(A60)
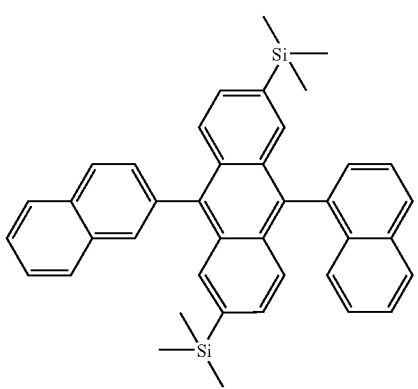
(A61)
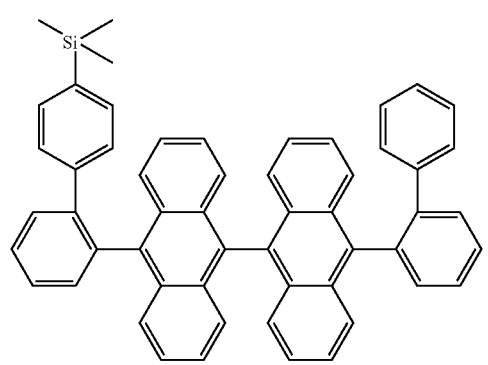
(A62)
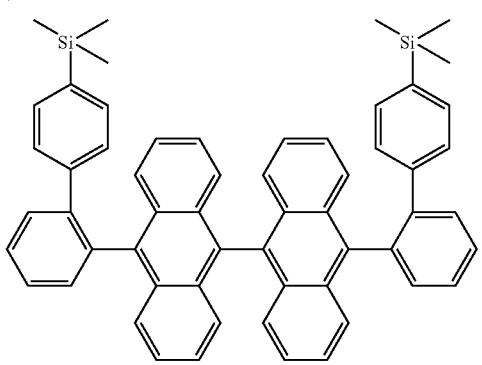

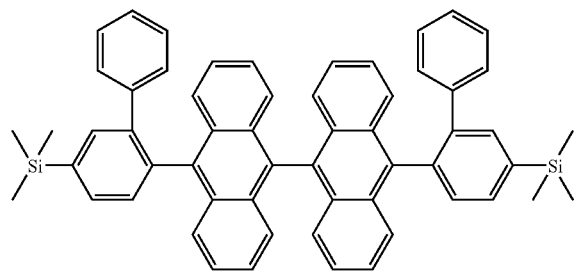

(A63)

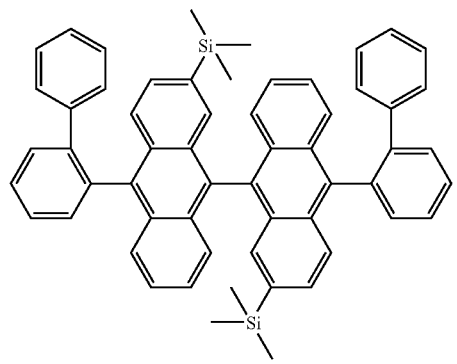

(A64)

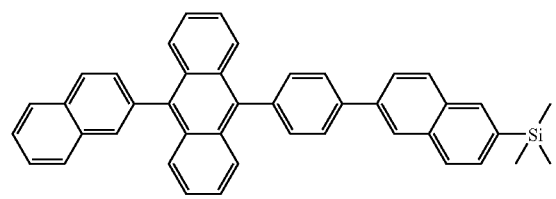

(A65)

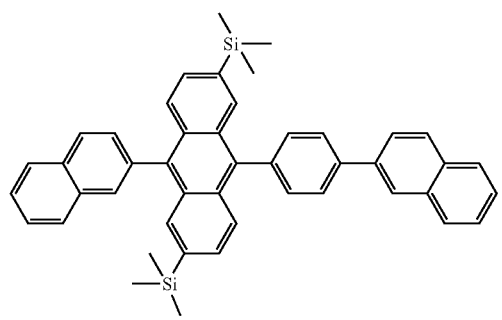

(A66)

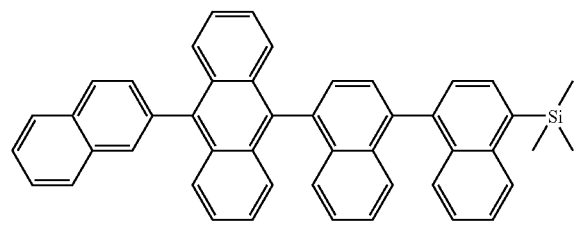

(A67)

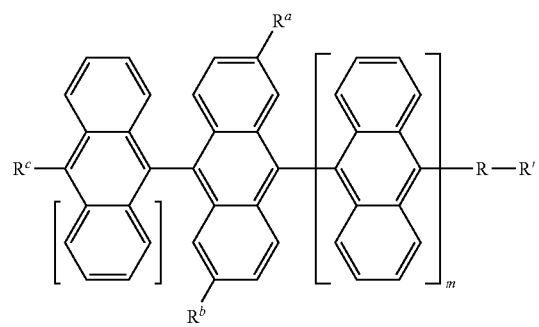

(A68)

Table 1 below indicates further preferred structures of the formula (1). Preference is likewise given here to the structures which, instead of groups of the formula Si(Me)$_3$, contain groups of the formula SiMe$_2$(t-Bu), SiMe(t-Bu)$_2$ or Si(i-Pr)$_3$. The symbols and indices used in the table relate to the formula (3) depicted below:

d=0 here means that the corresponding group is a 1-naphthyl group. Furthermore the abbreviation N(Ph)$_2$ in Table 1 stands for a diphenylamino groups N(p-Tol)$_2$ stands for a bis(para-tolyl)amino group and N(Ph)(1-Naph) stands for a N-phenyl-N-(1-naphthyl)amino group.

Formel (3)

TABLE 1

Preferred structures of the formula (3)

| No. | R | Ra | Rb | Rc | d | m | R' |
|---|---|---|---|---|---|---|---|
| 1 | Phenyl | H | H | Si(Me)3 | 0 | 0 | H |
| 2 | Phenyl | H | H | Si(Me)3 | 0 | 1 | H |
| 3 | Phenyl | H | H | Si(Me)3 | 1 | 0 | H |
| 4 | Phenyl | H | H | Si(Me)3 | 1 | 1 | H |
| 5 | Phenyl | H | Si(Me)3 | H | 0 | 0 | H |
| 6 | Phenyl | H | Si(Me)3 | H | 0 | 1 | H |
| 7 | Phenyl | H | Si(Me)3 | H | 1 | 0 | H |
| 8 | Phenyl | H | Si(Me)3 | H | 1 | 1 | H |
| 9 | Phenyl | H | Si(Me)3 | Si(Me)3 | 0 | 0 | H |
| 10 | Phenyl | H | Si(Me)3 | Si(Me)3 | 0 | 1 | H |
| 11 | Phenyl | H | Si(Me)3 | Si(Me)3 | 1 | 0 | H |
| 12 | Phenyl | H | Si(Me)3 | Si(Me)3 | 1 | 1 | H |

TABLE 1-continued

Preferred structures of the formula (3)

| No. | R | Ra | Rb | Rc | d | m | R' |
|---|---|---|---|---|---|---|---|
| 13 | Phenyl | H | Si(Me)3 | Methyl | 0 | 0 | H |
| 14 | Phenyl | H | Si(Me)3 | Methyl | 0 | 1 | H |
| 15 | Phenyl | H | Si(Me)3 | Methyl | 1 | 0 | H |
| 16 | Phenyl | H | Si(Me)3 | Methyl | 1 | 1 | H |
| 17 | Phenyl | H | Si(Me)3 | F | 0 | 0 | H |
| 18 | Phenyl | H | Si(Me)3 | F | 0 | 1 | H |
| 19 | Phenyl | H | Si(Me)3 | F | 1 | 0 | H |
| 20 | Phenyl | H | Si(Me)3 | F | 1 | 1 | H |
| 21 | Phenyl | H | Si(Me)3 | Phenyl | 0 | 0 | H |
| 22 | Phenyl | H | Si(Me)3 | Phenyl | 0 | 1 | H |
| 23 | Phenyl | H | Si(Me)3 | Phenyl | 1 | 0 | H |
| 24 | Phenyl | H | Si(Me)3 | Phenyl | 1 | 1 | H |
| 25 | Phenyl | Si(Me)3 | H | H | 0 | 0 | H |
| 26 | Phenyl | Si(Me)3 | H | H | 0 | 1 | H |
| 27 | Phenyl | Si(Me)3 | H | H | 1 | 0 | H |
| 28 | Phenyl | Si(Me)3 | H | H | 1 | 1 | H |
| 29 | Phenyl | Si(Me)3 | H | Si(Me)3 | 0 | 0 | H |
| 30 | Phenyl | Si(Me)3 | H | Si(Me)3 | 0 | 1 | H |
| 31 | Phenyl | Si(Me)3 | H | Si(Me)3 | 1 | 0 | H |
| 32 | Phenyl | Si(Me)3 | H | Si(Me)3 | 1 | 1 | H |
| 33 | Phenyl | Si(Me)3 | H | Methyl | 0 | 0 | H |
| 34 | Phenyl | Si(Me)3 | H | Methyl | 0 | 1 | H |
| 35 | Phenyl | Si(Me)3 | H | Methyl | 1 | 0 | H |
| 36 | Phenyl | Si(Me)3 | H | Methyl | 1 | 1 | H |
| 37 | Phenyl | Si(Me)3 | H | F | 0 | 0 | H |
| 38 | Phenyl | Si(Me)3 | H | F | 0 | 1 | H |
| 39 | Phenyl | Si(Me)3 | H | F | 1 | 0 | H |
| 40 | Phenyl | Si(Me)3 | H | F | 1 | 1 | H |
| 41 | Phenyl | Si(Me)3 | H | Phenyl | 0 | 0 | H |
| 42 | Phenyl | Si(Me)3 | H | Phenyl | 0 | 1 | H |
| 43 | Phenyl | Si(Me)3 | H | Phenyl | 1 | 0 | H |
| 44 | Phenyl | Si(Me)3 | H | Phenyl | 1 | 1 | H |
| 45 | Phenyl | Si(Me)3 | Si(Me)3 | H | 0 | 0 | H |
| 46 | Phenyl | Si(Me)3 | Si(Me)3 | H | 0 | 1 | H |
| 47 | Phenyl | Si(Me)3 | Si(Me)3 | H | 1 | 0 | H |
| 48 | Phenyl | Si(Me)3 | Si(Me)3 | H | 1 | 1 | H |
| 49 | Phenyl | Si(Me)3 | Si(Me)3 | Si(Me)3 | 0 | 0 | H |
| 50 | Phenyl | Si(Me)3 | Si(Me)3 | Si(Me)3 | 0 | 1 | H |
| 51 | Phenyl | Si(Me)3 | Si(Me)3 | Si(Me)3 | 1 | 0 | H |
| 52 | Phenyl | Si(Me)3 | Si(Me)3 | Si(Me)3 | 1 | 1 | H |
| 53 | Phenyl | Si(Me)3 | Si(Me)3 | Methyl | 0 | 0 | H |
| 54 | Phenyl | Si(Me)3 | Si(Me)3 | Methyl | 0 | 1 | H |
| 55 | Phenyl | Si(Me)3 | Si(Me)3 | Methyl | 1 | 0 | H |
| 56 | Phenyl | Si(Me)3 | Si(Me)3 | Methyl | 1 | 1 | H |
| 57 | Phenyl | Si(Me)3 | Si(Me)3 | F | 0 | 0 | H |
| 58 | Phenyl | Si(Me)3 | Si(Me)3 | F | 0 | 1 | H |
| 59 | Phenyl | Si(Me)3 | Si(Me)3 | F | 1 | 0 | H |
| 60 | Phenyl | Si(Me)3 | Si(Me)3 | F | 1 | 1 | H |
| 61 | Phenyl | Si(Me)3 | Si(Me)3 | Phenyl | 0 | 0 | H |
| 62 | Phenyl | Si(Me)3 | Si(Me)3 | Phenyl | 0 | 1 | H |
| 63 | Phenyl | Si(Me)3 | Si(Me)3 | Phenyl | 1 | 0 | H |
| 64 | Phenyl | Si(Me)3 | Si(Me)3 | Phenyl | 1 | 1 | H |
| 65 | Phenyl | H | H | H | 0 | 0 | Si(Me)3 |
| 66 | Phenyl | H | H | H | 0 | 1 | Si(Me)3 |
| 67 | Phenyl | H | H | H | 1 | 0 | Si(Me)3 |
| 68 | Phenyl | H | H | H | 1 | 1 | Si(Me)3 |
| 69 | Phenyl | H | H | Si(Me)3 | 0 | 0 | Si(Me)3 |
| 70 | Phenyl | H | H | Si(Me)3 | 0 | 1 | Si(Me)3 |
| 71 | Phenyl | H | H | Si(Me)3 | 1 | 0 | Si(Me)3 |
| 72 | Phenyl | H | H | Si(Me)3 | 1 | 1 | Si(Me)3 |
| 73 | Phenyl | H | H | Methyl | 0 | 0 | Si(Me)3 |
| 74 | Phenyl | H | H | Methyl | 0 | 1 | Si(Me)3 |
| 75 | Phenyl | H | H | Methyl | 1 | 0 | Si(Me)3 |
| 76 | Phenyl | H | H | Methyl | 1 | 1 | Si(Me)3 |
| 77 | Phenyl | H | H | F | 0 | 0 | Si(Me)3 |
| 78 | Phenyl | H | H | F | 0 | 1 | Si(Me)3 |
| 79 | Phenyl | H | H | F | 1 | 0 | Si(Me)3 |
| 80 | Phenyl | H | H | F | 1 | 1 | Si(Me)3 |
| 81 | Phenyl | H | H | Phenyl | 0 | 0 | Si(Me)3 |
| 82 | Phenyl | H | H | Phenyl | 0 | 1 | Si(Me)3 |
| 83 | Phenyl | H | H | Phenyl | 1 | 0 | Si(Me)3 |
| 84 | Phenyl | H | H | Phenyl | 1 | 1 | Si(Me)3 |
| 85 | Phenyl | H | Si(Me)3 | H | 0 | 0 | Si(Me)3 |
| 86 | Phenyl | H | Si(Me)3 | H | 0 | 1 | Si(Me)3 |
| 87 | Phenyl | H | Si(Me)3 | H | 1 | 0 | Si(Me)3 |
| 88 | Phenyl | H | Si(Me)3 | H | 1 | 1 | Si(Me)3 |
| 89 | Phenyl | H | Si(Me)3 | Si(Me)3 | 0 | 0 | Si(Me)3 |
| 90 | Phenyl | H | Si(Me)3 | Si(Me)3 | 0 | 1 | Si(Me)3 |
| 91 | Phenyl | H | Si(Me)3 | Si(Me)3 | 1 | 0 | Si(Me)3 |
| 92 | Phenyl | H | Si(Me)3 | Si(Me)3 | 1 | 1 | Si(Me)3 |
| 93 | Phenyl | H | Si(Me)3 | Methyl | 0 | 0 | Si(Me)3 |
| 94 | Phenyl | H | Si(Me)3 | Methyl | 0 | 1 | Si(Me)3 |
| 95 | Phenyl | H | Si(Me)3 | Methyl | 1 | 0 | Si(Me)3 |
| 96 | Phenyl | H | Si(Me)3 | Methyl | 1 | 1 | Si(Me)3 |
| 97 | Phenyl | H | Si(Me)3 | F | 0 | 0 | Si(Me)3 |
| 98 | Phenyl | H | Si(Me)3 | F | 0 | 1 | Si(Me)3 |
| 99 | Phenyl | H | Si(Me)3 | F | 1 | 0 | Si(Me)3 |
| 100 | Phenyl | H | Si(Me)3 | F | 1 | 1 | Si(Me)3 |
| 101 | Phenyl | H | Si(Me)3 | Phenyl | 0 | 0 | Si(Me)3 |
| 102 | Phenyl | H | Si(Me)3 | Phenyl | 0 | 1 | Si(Me)3 |
| 103 | Phenyl | H | Si(Me)3 | Phenyl | 1 | 0 | Si(Me)3 |
| 104 | Phenyl | H | Si(Me)3 | Phenyl | 1 | 1 | Si(Me)3 |
| 105 | Phenyl | Si(Me)3 | H | H | 0 | 0 | Si(Me)3 |
| 106 | Phenyl | Si(Me)3 | H | H | 0 | 1 | Si(Me)3 |
| 107 | Phenyl | Si(Me)3 | H | H | 1 | 0 | Si(Me)3 |
| 108 | Phenyl | Si(Me)3 | H | H | 1 | 1 | Si(Me)3 |
| 109 | Phenyl | Si(Me)3 | H | Si(Me)3 | 0 | 0 | Si(Me)3 |
| 110 | Phenyl | Si(Me)3 | H | Si(Me)3 | 0 | 1 | Si(Me)3 |
| 111 | Phenyl | Si(Me)3 | H | Si(Me)3 | 1 | 0 | Si(Me)3 |
| 112 | Phenyl | Si(Me)3 | H | Si(Me)3 | 1 | 1 | Si(Me)3 |
| 113 | Phenyl | Si(Me)3 | H | Methyl | 0 | 0 | Si(Me)3 |
| 114 | Phenyl | Si(Me)3 | H | Methyl | 0 | 1 | Si(Me)3 |
| 115 | Phenyl | Si(Me)3 | H | Methyl | 1 | 0 | Si(Me)3 |
| 116 | Phenyl | Si(Me)3 | H | Methyl | 1 | 1 | Si(Me)3 |
| 117 | Phenyl | Si(Me)3 | H | F | 0 | 0 | Si(Me)3 |
| 118 | Phenyl | Si(Me)3 | H | F | 0 | 1 | Si(Me)3 |
| 119 | Phenyl | Si(Me)3 | H | F | 1 | 0 | Si(Me)3 |
| 120 | Phenyl | Si(Me)3 | H | F | 1 | 1 | Si(Me)3 |
| 121 | Phenyl | Si(Me)3 | H | Phenyl | 0 | 0 | Si(Me)3 |
| 122 | Phenyl | Si(Me)3 | H | Phenyl | 0 | 1 | Si(Me)3 |
| 123 | Phenyl | Si(Me)3 | H | Phenyl | 1 | 0 | Si(Me)3 |
| 124 | Phenyl | Si(Me)3 | H | Phenyl | 1 | 1 | Si(Me)3 |
| 125 | Phenyl | Si(Me)3 | Si(Me)3 | H | 0 | 0 | Si(Me)3 |
| 126 | Phenyl | Si(Me)3 | Si(Me)3 | H | 0 | 1 | Si(Me)3 |
| 127 | Phenyl | Si(Me)3 | Si(Me)3 | H | 1 | 0 | Si(Me)3 |
| 128 | Phenyl | Si(Me)3 | Si(Me)3 | H | 1 | 1 | Si(Me)3 |
| 129 | Phenyl | Si(Me)3 | Si(Me)3 | Si(Me)3 | 0 | 0 | Si(Me)3 |
| 130 | Phenyl | Si(Me)3 | Si(Me)3 | Si(Me)3 | 0 | 1 | Si(Me)3 |
| 131 | Phenyl | Si(Me)3 | Si(Me)3 | Si(Me)3 | 1 | 0 | Si(Me)3 |
| 132 | Phenyl | Si(Me)3 | Si(Me)3 | Si(Me)3 | 1 | 1 | Si(Me)3 |
| 133 | Phenyl | Si(Me)3 | Si(Me)3 | Methyl | 0 | 0 | Si(Me)3 |
| 134 | Phenyl | Si(Me)3 | Si(Me)3 | Methyl | 0 | 1 | Si(Me)3 |
| 135 | Phenyl | Si(Me)3 | Si(Me)3 | Methyl | 1 | 0 | Si(Me)3 |
| 136 | Phenyl | Si(Me)3 | Si(Me)3 | Methyl | 1 | 1 | Si(Me)3 |
| 137 | Phenyl | Si(Me)3 | Si(Me)3 | F | 0 | 0 | Si(Me)3 |
| 138 | Phenyl | Si(Me)3 | Si(Me)3 | F | 0 | 1 | Si(Me)3 |
| 139 | Phenyl | Si(Me)3 | Si(Me)3 | F | 1 | 0 | Si(Me)3 |
| 140 | Phenyl | Si(Me)3 | Si(Me)3 | F | 1 | 1 | Si(Me)3 |
| 141 | Phenyl | Si(Me)3 | Si(Me)3 | Phenyl | 0 | 0 | Si(Me)3 |
| 142 | Phenyl | Si(Me)3 | Si(Me)3 | Phenyl | 0 | 1 | Si(Me)3 |
| 143 | Phenyl | Si(Me)3 | Si(Me)3 | Phenyl | 1 | 0 | Si(Me)3 |
| 144 | Phenyl | Si(Me)3 | Si(Me)3 | Phenyl | 1 | 1 | Si(Me)3 |
| 145 | 1-Naphthyl | H | H | Si(Me)3 | 0 | 0 | H |
| 146 | 1-Naphthyl | H | H | Si(Me)3 | 0 | 1 | H |
| 147 | 1-Naphthyl | H | H | Si(Me)3 | 1 | 0 | H |
| 148 | 1-Naphthyl | H | H | Si(Me)3 | 1 | 1 | H |
| 149 | 1-Naphthyl | H | Si(Me)3 | H | 0 | 0 | H |
| 150 | 1-Naphthyl | H | Si(Me)3 | H | 0 | 1 | H |
| 151 | 1-Naphthyl | H | Si(Me)3 | H | 1 | 0 | H |
| 152 | 1-Naphthyl | H | Si(Me)3 | H | 1 | 1 | H |
| 153 | 1-Naphthyl | H | Si(Me)3 | Si(Me)3 | 0 | 0 | H |
| 154 | 1-Naphthyl | H | Si(Me)3 | Si(Me)3 | 0 | 1 | H |
| 155 | 1-Naphthyl | H | Si(Me)3 | Si(Me)3 | 1 | 0 | H |
| 156 | 1-Naphthyl | H | Si(Me)3 | Si(Me)3 | 1 | 1 | H |
| 157 | 1-Naphthyl | H | Si(Me)3 | Methyl | 0 | 0 | H |
| 158 | 1-Naphthyl | H | Si(Me)3 | Methyl | 0 | 1 | H |
| 159 | 1-Naphthyl | H | Si(Me)3 | Methyl | 1 | 0 | H |
| 160 | 1-Naphthyl | H | Si(Me)3 | Methyl | 1 | 1 | H |
| 161 | 1-Naphthyl | H | Si(Me)3 | F | 0 | 0 | H |
| 162 | 1-Naphthyl | H | Si(Me)3 | F | 0 | 1 | H |
| 163 | 1-Naphthyl | H | Si(Me)3 | F | 1 | 0 | H |
| 164 | 1-Naphthyl | H | Si(Me)3 | F | 1 | 1 | H |

TABLE 1-continued

Preferred structures of the formula (3)

| No. | R | Ra | Rb | Rc | d | m | R' |
|---|---|---|---|---|---|---|---|
| 165 | 1-Naphthyl | H | Si(Me)3 | Phenyl | 0 | 0 | H |
| 166 | 1-Naphthyl | H | Si(Me)3 | Phenyl | 0 | 1 | H |
| 167 | 1-Naphthyl | H | Si(Me)3 | Phenyl | 1 | 0 | H |
| 168 | 1-Naphthyl | H | Si(Me)3 | Phenyl | 1 | 1 | H |
| 169 | 1-Naphthyl | Si(Me)3 | H | H | 0 | 0 | H |
| 170 | 1-Naphthyl | Si(Me)3 | H | H | 0 | 1 | H |
| 171 | 1-Naphthyl | Si(Me)3 | H | H | 1 | 0 | H |
| 172 | 1-Naphthyl | Si(Me)3 | H | H | 1 | 1 | H |
| 173 | 1-Naphthyl | Si(Me)3 | H | Si(Me)3 | 0 | 0 | H |
| 174 | 1-Naphthyl | Si(Me)3 | H | Si(Me)3 | 0 | 1 | H |
| 175 | 1-Naphthyl | Si(Me)3 | H | Si(Me)3 | 1 | 0 | H |
| 176 | 1-Naphthyl | Si(Me)3 | H | Si(Me)3 | 1 | 1 | H |
| 177 | 1-Naphthyl | Si(Me)3 | H | Methyl | 0 | 0 | H |
| 178 | 1-Naphthyl | Si(Me)3 | H | Methyl | 0 | 1 | H |
| 179 | 1-Naphthyl | Si(Me)3 | H | Methyl | 1 | 0 | H |
| 180 | 1-Naphthyl | Si(Me)3 | H | Methyl | 1 | 1 | H |
| 181 | 1-Naphthyl | Si(Me)3 | H | F | 0 | 0 | H |
| 182 | 1-Naphthyl | i(Me)3 | H | F | 0 | 1 | H |
| 183 | 1-Naphthyl | Si(Me)3 | H | F | 1 | 0 | H |
| 184 | 1-Naphthyl | Si(Me)3 | H | F | 1 | 1 | H |
| 185 | 1-Naphthyl | Si(Me)3 | H | Phenyl | 0 | 0 | H |
| 186 | 1-Naphthyl | Si(Me)3 | H | Phenyl | 0 | 1 | H |
| 187 | 1-Naphthyl | Si(Me)3 | H | Phenyl | 1 | 0 | H |
| 188 | 1-Naphthyl | Si(Me)3 | H | Phenyl | 1 | 1 | H |
| 189 | 1-Naphthyl | Si(Me)3 | Si(Me)3 | H | 0 | 0 | H |
| 190 | 1-Naphthyl | Si(Me)3 | Si(Me)3 | H | 0 | 1 | H |
| 191 | 1-Naphthyl | Si(Me)3 | Si(Me)3 | H | 1 | 0 | H |
| 192 | 1-Naphthyl | Si(Me)3 | Si(Me)3 | H | 1 | 1 | H |
| 193 | 1-Naphthyl | Si(Me)3 | Si(Me)3 | Si(Me)3 | 0 | 0 | H |
| 194 | 1-Naphthyl | Si(Me)3 | Si(Me)3 | Si(Me)3 | 0 | 1 | H |
| 195 | 1-Naphthyl | Si(Me)3 | Si(Me)3 | Si(Me)3 | 1 | 0 | H |
| 196 | 1-Naphthyl | Si(Me)3 | Si(Me)3 | Si(Me)3 | 1 | 1 | H |
| 197 | 1-Naphthyl | Si(Me)3 | Si(Me)3 | Methyl | 0 | 0 | H |
| 198 | 1-Naphthyl | Si(Me)3 | Si(Me)3 | Methyl | 0 | 1 | H |
| 199 | 1-Naphthyl | Si(Me)3 | Si(Me)3 | Methyl | 1 | 0 | H |
| 200 | 1-Naphthyl | Si(Me)3 | Si(Me)3 | Methyl | 1 | 1 | H |
| 201 | 1-Naphthyl | Si(Me)3 | Si(Me)3 | F | 0 | 0 | H |
| 202 | 1-Naphthyl | Si(Me)3 | Si(Me)3 | F | 0 | 1 | H |
| 203 | 1-Naphthyl | Si(Me)3 | Si(Me)3 | F | 1 | 0 | H |
| 204 | 1-Naphthyl | Si(Me)3 | Si(Me)3 | F | 1 | 1 | H |
| 205 | 1-Naphthyl | Si(Me)3 | Si(Me)3 | Phenyl | 0 | 0 | H |
| 206 | 1-Naphthyl | Si(Me)3 | Si(Me)3 | Phenyl | 0 | 1 | H |
| 207 | 1-Naphthyl | Si(Me)3 | Si(Me)3 | Phenyl | 1 | 0 | H |
| 208 | 1-Naphthyl | Si(Me)3 | Si(Me)3 | Phenyl | 1 | 1 | H |
| 209 | 1-Naphthyl | H | H | H | 0 | 0 | Si(Me)3 |
| 210 | 1-Naphthyl | H | H | H | 0 | 1 | Si(Me)3 |
| 211 | 1-Naphthyl | H | H | H | 1 | 0 | Si(Me)3 |
| 212 | 1-Naphthyl | H | H | H | 1 | 1 | Si(Me)3 |
| 213 | 1-Naphthyl | H | H | Si(Me)3 | 0 | 0 | Si(Me)3 |
| 214 | 1-Naphthyl | H | H | Si(Me)3 | 0 | 1 | Si(Me)3 |
| 215 | 1-Naphthyl | H | H | Si(Me)3 | 1 | 0 | Si(Me)3 |
| 216 | 1-Naphthyl | H | H | Si(Me)3 | 1 | 1 | Si(Me)3 |
| 217 | 1-Naphthyl | H | H | Methyl | 0 | 0 | Si(Me)3 |
| 218 | 1-Naphthyl | H | H | Methyl | 0 | 1 | Si(Me)3 |
| 219 | 1-Naphthyl | H | H | Methyl | 1 | 0 | Si(Me)3 |
| 220 | 1-Naphthyl | H | H | Methyl | 1 | 1 | Si(Me)3 |
| 221 | 1-Naphthyl | H | H | F | 0 | 0 | Si(Me)3 |
| 222 | 1-Naphthyl | H | H | F | 0 | 1 | Si(Me)3 |
| 223 | 1-Naphthyl | H | H | F | 1 | 0 | Si(Me)3 |
| 224 | 1-Naphthyl | H | H | F | 1 | 1 | Si(Me)3 |
| 225 | 1-Naphthyl | H | H | Phenyl | 0 | 0 | Si(Me)3 |
| 226 | 1-Naphthyl | H | H | Phenyl | 0 | 1 | Si(Me)3 |
| 227 | 1-Naphthyl | H | H | Phenyl | 1 | 0 | Si(Me)3 |
| 228 | 1-Naphthyl | H | H | Phenyl | 1 | 1 | Si(Me)3 |
| 229 | 1-Naphthyl | H | Si(Me)3 | H | 0 | 0 | Si(Me)3 |
| 230 | 1-Naphthyl | H | Si(Me)3 | H | 0 | 1 | Si(Me)3 |
| 231 | 1-Naphthyl | H | Si(Me)3 | H | 1 | 0 | Si(Me)3 |
| 232 | 1-Naphthyl | H | Si(Me)3 | H | 1 | 1 | Si(Me)3 |
| 233 | 1-Naphthyl | H | Si(Me)3 | Si(Me)3 | 0 | 0 | Si(Me)3 |
| 234 | 1-Naphthyl | H | Si(Me)3 | Si(Me)3 | 0 | 1 | Si(Me)3 |
| 235 | 1-Naphthyl | H | Si(Me)3 | Si(Me)3 | 1 | 0 | Si(Me)3 |
| 236 | 1-Naphthyl | H | Si(Me)3 | Si(Me)3 | 1 | 1 | Si(Me)3 |
| 237 | 1-Naphthyl | H | Si(Me)3 | Methyl | 0 | 0 | Si(Me)3 |
| 238 | 1-Naphthyl | H | Si(Me)3 | Methyl | 0 | 1 | Si(Me)3 |
| 239 | 1-Naphthyl | H | Si(Me)3 | Methyl | 1 | 0 | Si(Me)3 |
| 240 | 1-Naphthyl | H | Si(Me)3 | Methyl | 1 | 1 | Si(Me)3 |
| 241 | 1-Naphthyl | H | Si(Me)3 | F | 0 | 0 | Si(Me)3 |
| 242 | 1-Naphthyl | H | Si(Me)3 | F | 0 | 1 | Si(Me)3 |
| 243 | 1-Naphthyl | H | Si(Me)3 | F | 1 | 0 | Si(Me)3 |
| 244 | 1-Naphthyl | H | Si(Me)3 | F | 1 | 1 | Si(Me)3 |
| 245 | 1-Naphthyl | H | Si(Me)3 | Phenyl | 0 | 0 | Si(Me)3 |
| 246 | 1-Naphthyl | H | Si(Me)3 | Phenyl | 0 | 1 | Si(Me)3 |
| 247 | 1-Naphthyl | H | Si(Me)3 | Phenyl | 1 | 0 | Si(Me)3 |
| 248 | 1-Naphthyl | H | Si(Me)3 | Phenyl | 1 | 1 | Si(Me)3 |
| 249 | 1-Naphthyl | Si(Me)3 | H | H | 0 | 0 | Si(Me)3 |
| 250 | 1-Naphthyl | Si(Me)3 | H | H | 0 | 1 | Si(Me)3 |
| 251 | 1-Naphthyl | Si(Me)3 | H | H | 1 | 0 | Si(Me)3 |
| 252 | 1-Naphthyl | Si(Me)3 | H | H | 1 | 1 | Si(Me)3 |
| 253 | 1-Naphthyl | Si(Me)3 | H | Si(Me)3 | 0 | 0 | Si(Me)3 |
| 254 | 1-Naphthyl | Si(Me)3 | H | Si(Me)3 | 0 | 1 | Si(Me)3 |
| 255 | 1-Naphthyl | Si(Me)3 | H | Si(Me)3 | 1 | 0 | Si(Me)3 |
| 256 | 1-Naphthyl | Si(Me)3 | H | Si(Me)3 | 1 | 1 | Si(Me)3 |
| 257 | 1-Naphthyl | Si(Me)3 | H | Methyl | 0 | 0 | Si(Me)3 |
| 258 | 1-Naphthyl | Si(Me)3 | H | Methyl | 0 | 1 | Si(Me)3 |
| 259 | 1-Naphthyl | Si(Me)3 | H | Methyl | 1 | 0 | Si(Me)3 |
| 260 | 1-Naphthyl | Si(Me)3 | H | Methyl | 1 | 1 | Si(Me)3 |
| 261 | 1-Naphthyl | Si(Me)3 | H | F | 0 | 0 | Si(Me)3 |
| 262 | 1-Naphthyl | Si(Me)3 | H | F | 0 | 1 | Si(Me)3 |
| 263 | 1-Naphthyl | Si(Me)3 | H | F | 1 | 0 | Si(Me)3 |
| 264 | 1-Naphthyl | Si(Me)3 | H | F | 1 | 1 | Si(Me)3 |
| 265 | 1-Naphthyl | Si(Me)3 | H | Phenl | 0 | 0 | Si(Me)3 |
| 266 | 1-Naphthyl | Si(Me)3 | H | Phenyl | 0 | 1 | Si(Me)3 |
| 267 | 1-Naphthyl | Si(Me)3 | H | Phenyl | 1 | 0 | Si(Me)3 |
| 268 | 1-Naphthyl | Si(Me)3 | H | Phenyl | 1 | 1 | Si(Me)3 |
| 269 | 1-Naphthyl | Si(Me)3 | Si(Me)3 | H | 0 | 0 | Si(Me)3 |
| 270 | 1-Naphthyl | Si(Me)3 | Si(Me)3 | H | 0 | 1 | Si(Me)3 |
| 271 | 1-Naphthyl | Si(Me)3 | Si(Me)3 | H | 1 | 0 | Si(Me)3 |
| 272 | 1-Naphthyl | Si(Me)3 | Si(Me)3 | H | 1 | 1 | Si(Me)3 |
| 273 | 1-Naphthyl | Si(Me)3 | Si(Me)3 | Si(Me)3 | 0 | 0 | Si(Me)3 |
| 274 | 1-Naphthyl | Si(Me)3 | Si(Me)3 | Si(Me)3 | 0 | 1 | Si(Me)3 |
| 275 | 1-Naphthyl | Si(Me)3 | Si(Me)3 | Si(Me)3 | 1 | 0 | Si(Me)3 |
| 276 | 1-Naphthyl | Si(Me)3 | Si(Me)3 | Si(Me)3 | 1 | 1 | Si(Me)3 |
| 277 | 1-Naphthyl | Si(Me)3 | Si(Me)3 | Methyl | 0 | 0 | Si(Me)3 |
| 278 | 1-Naphthyl | Si(Me)3 | Si(Me)3 | Methyl | 0 | 1 | Si(Me)3 |
| 279 | 1-Naphthyl | Si(Me)3 | Si(Me)3 | Methyl | 1 | 0 | Si(Me)3 |
| 280 | 1-Naphthyl | Si(Me)3 | Si(Me)3 | Methyl | 1 | 1 | Si(Me)3 |
| 281 | 1-Naphthyl | Si(Me)3 | Si(Me)3 | F | 0 | 0 | Si(Me)3 |
| 282 | 1-Naphthyl | Si(Me)3 | Si(Me)3 | F | 0 | 1 | Si(Me)3 |
| 283 | 1-Naphthyl | Si(Me)3 | Si(Me)3 | F | 1 | 0 | Si(Me)3 |
| 284 | 1-Naphthyl | Si(Me)3 | Si(Me)3 | F | 1 | 1 | Si(Me)3 |
| 285 | 1-Naphthyl | Si(Me)3 | Si(Me)3 | Phenyl | 0 | 0 | Si(Me)3 |
| 286 | 1-Naphthyl | Si(Me)3 | Si(Me)3 | Phenyl | 0 | 1 | Si(Me)3 |
| 287 | 1-Naphthyl | Si(Me)3 | Si(Me)3 | Phenyl | 1 | 0 | Si(Me)3 |
| 288 | 1-Naphthyl | Si(Me)3 | Si(Me)3 | Phenyl | 1 | 1 | Si(Me)3 |
| 289 | 2-Naphthyl | H | H | Si(Me)3 | 0 | 0 | H |
| 290 | 2-Naphthyl | H | H | Si(Me)3 | 0 | 1 | H |
| 291 | 2-Naphthyl | H | H | Si(Me)3 | 1 | 0 | H |
| 292 | 2-Naphthyl | H | H | Si(Me)3 | 1 | 1 | H |
| 293 | 2-Naphthyl | H | Si(Me)3 | H | 0 | 0 | H |
| 294 | 2-Naphthyl | H | Si(Me)3 | H | 0 | 1 | H |
| 295 | 2-Naphthyl | H | Si(Me)3 | H | 1 | 0 | H |
| 296 | 2-Naphthyl | H | Si(Me)3 | H | 1 | 1 | H |
| 297 | 2-Naphthyl | H | Si(Me)3 | Si(Me)3 | 0 | 0 | H |
| 298 | 2-Naphthyl | H | Si(Me)3 | Si(Me)3 | 0 | 1 | H |
| 299 | 2-Naphthyl | H | Si(Me)3 | Si(Me)3 | 1 | 0 | H |
| 300 | 2-Naphthyl | H | Si(Me)3 | Si(Me)3 | 1 | 1 | H |
| 301 | 2-Naphthyl | H | Si(Me)3 | Methyl | 0 | 0 | H |
| 302 | 2-Naphthyl | H | Si(Me)3 | Methyl | 0 | 1 | H |
| 303 | 2-Naphthyl | H | Si(Me)3 | Methyl | 1 | 0 | H |
| 304 | 2-Naphthyl | H | Si(Me)3 | Methyl | 1 | 1 | H |
| 305 | 2-Naphthyl | H | Si(Me)3 | F | 0 | 0 | H |
| 306 | 2-Naphthyl | H | Si(Me)3 | F | 0 | 1 | H |
| 307 | 2-Naphthyl | H | Si(Me)3 | F | 1 | 0 | H |
| 308 | 2-Naphthyl | H | Si(Me)3 | F | 1 | 1 | H |
| 309 | 2-Naphthyl | H | Si(Me)3 | Phenyl | 0 | 0 | H |
| 310 | 2-Naphthyl | H | Si(Me)3 | Phenyl | 0 | 1 | H |
| 311 | 2-Naphthyl | H | Si(Me)3 | Phenyl | 1 | 0 | H |
| 312 | 2-Naphthyl | H | Si(Me)3 | Phenyl | 1 | 1 | H |
| 313 | 2-Naphthyl | Si(Me)3 | H | H | 0 | 0 | H |
| 314 | 2-Naphthyl | Si(Me)3 | H | H | 0 | 1 | H |
| 315 | 2-Naphthyl | Si(Me)3 | H | H | 1 | 0 | H |
| 316 | 2-Naphthyl | Si(Me)3 | H | H | 1 | 1 | H |

TABLE 1-continued

Preferred structures of the formula (3)

| No. | R | Ra | Rb | Rc | d | m | R' |
|---|---|---|---|---|---|---|---|
| 317 | 2-Naphthyl | Si(Me)3 | H | Si(Me)3 | 0 | 0 | H |
| 318 | 2-Naphthyl | Si(Me)3 | H | Si(Me)3 | 0 | 1 | H |
| 319 | 2-Naphthyl | Si(Me)3 | H | Si(Me)3 | 1 | 0 | H |
| 320 | 2-Naphthyl | Si(Me)3 | H | Si(Me)3 | 1 | 1 | H |
| 321 | 2-Naphthyl | Si(Me)3 | H | Methyl | 0 | 0 | H |
| 322 | 2-Naphthyl | Si(Me)3 | H | Methyl | 0 | 1 | H |
| 323 | 2-Naphthyl | Si(Me)3 | H | Methyl | 1 | 0 | H |
| 324 | 2-Naphthyl | Si(Me)3 | H | Methyl | 1 | 1 | H |
| 325 | 2-Naphthyl | Si(Me)3 | H | F | 0 | 0 | H |
| 326 | 2-Naphthyl | Si(Me)3 | H | F | 0 | 1 | H |
| 327 | 2-Naphthyl | Si(Me)3 | H | F | 1 | 0 | H |
| 328 | 2-Naphthyl | Si(Me)3 | H | F | 1 | 1 | H |
| 329 | 2-Naphthyl | Si(Me)3 | H | Phenyl | 0 | 0 | H |
| 330 | 2-Naphthyl | Si(Me)3 | H | Phenyl | 0 | 1 | H |
| 331 | 2-Naphthyl | Si(Me)3 | H | Phenyl | 1 | 0 | H |
| 332 | 2-Naphthyl | Si(Me)3 | H | Phenyl | 1 | 1 | H |
| 333 | 2-Naphthyl | Si(Me)3 | Si(Me)3 | H | 0 | 0 | H |
| 334 | 2-Naphthyl | Si(Me)3 | Si(Me)3 | H | 0 | 1 | H |
| 335 | 2-Naphthyl | Si(Me)3 | Si(Me)3 | H | 1 | 0 | H |
| 336 | 2-Naphthyl | Si(Me)3 | Si(Me)3 | H | 1 | 1 | H |
| 337 | 2-Naphthyl | Si(Me)3 | Si(Me)3 | Si(Me)3 | 0 | 0 | H |
| 338 | 2-Naphthyl | Si(Me)3 | Si(Me)3 | Si(Me)3 | 0 | 1 | H |
| 339 | 2-Naphthyl | Si(Me)3 | Si(Me)3 | Si(Me)3 | 1 | 0 | H |
| 340 | 2-Naphthyl | Si(Me)3 | Si(Me)3 | Si(Me)3 | 1 | 1 | H |
| 341 | 2-Naphthyl | Si(Me)3 | Si(Me)3 | Methyl | 0 | 0 | H |
| 342 | 2-Naphthyl | Si(Me)3 | Si(Me)3 | Methyl | 0 | 1 | H |
| 343 | 2-Naphthyl | Si(Me)3 | Si(Me)3 | Methyl | 1 | 0 | H |
| 344 | 2-Naphthyl | Si(Me)3 | Si(Me)3 | Methyl | 1 | 1 | H |
| 345 | 2-Naphthyl | Si(Me)3 | Si(Me)3 | F | 0 | 0 | H |
| 346 | 2-Naphthyl | Si(Me)3 | Si(Me)3 | F | 0 | 1 | H |
| 347 | 2-Naphthyl | Si(Me)3 | Si(Me)3 | F | 1 | 0 | H |
| 348 | 2-Naphthyl | Si(Me)3 | Si(Me)3 | F | 1 | 1 | H |
| 349 | 2-Naphthyl | Si(Me)3 | Si(Me)3 | Phenyl | 0 | 0 | H |
| 350 | 2-Naphthyl | Si(Me)3 | Si(Me)3 | Phenyl | 0 | 1 | H |
| 351 | 2-Naphthyl | Si(Me)3 | Si(Me)3 | Phenyl | 1 | 0 | H |
| 352 | 2-Naphthyl | Si(Me)3 | Si(Me)3 | Phenyl | 1 | 1 | H |
| 353 | 2-Naphthyl | H | H | H | 0 | 0 | Si(Me)3 |
| 354 | 2-Naphthyl | H | H | H | 0 | 1 | Si(Me)3 |
| 355 | 2-Naphthyl | H | H | H | 1 | 0 | Si(Me)3 |
| 356 | 2-Naphthyl | H | H | H | 1 | 1 | Si(Me)3 |
| 357 | 2-Naphthyl | H | H | Si(Me)3 | 0 | 0 | Si(Me)3 |
| 358 | 2-Naphthyl | H | H | Si(Me)3 | 0 | 1 | Si(Me)3 |
| 359 | 2-Naphthyl | H | H | Si(Me)3 | 1 | 0 | Si(Me)3 |
| 360 | 2-Naphthyl | H | H | Si(Me)3 | 1 | 1 | Si(Me)3 |
| 361 | 2-Naphthyl | H | H | Methyl | 0 | 0 | Si(Me)3 |
| 362 | 2-Naphthyl | H | H | Methyl | 0 | 1 | Si(Me)3 |
| 363 | 2-Naphthyl | H | H | Methyl | 1 | 0 | Si(Me)3 |
| 364 | 2-Naphthyl | H | H | Methyl | 1 | 1 | Si(Me)3 |
| 365 | 2-Naphthyl | H | H | F | 0 | 0 | Si(Me)3 |
| 366 | 2-Naphthyl | H | H | F | 0 | 1 | Si(Me)3 |
| 367 | 2-Naphthyl | H | H | F | 1 | 0 | Si(Me)3 |
| 368 | 2-Naphthyl | H | H | F | 1 | 1 | Si(Me)3 |
| 369 | 2-Naphthyl | H | H | Phenyl | 0 | 0 | Si(Me)3 |
| 370 | 2-Naphthyl | H | H | Phenyl | 0 | 1 | Si(Me)3 |
| 371 | 2-Naphthyl | H | H | Phenyl | 1 | 0 | Si(Me)3 |
| 372 | 2-Naphthyl | H | H | Phenyl | 1 | 1 | Si(Me)3 |
| 373 | 2-Naphthyl | H | Si(Me)3 | H | 0 | 0 | Si(Me)3 |
| 374 | 2-Naphthyl | H | Si(Me)3 | H | 0 | 1 | Si(Me)3 |
| 375 | 2-Naphthyl | H | Si(Me)3 | H | 1 | 0 | Si(Me)3 |
| 376 | 2-Naphthyl | H | Si(Me)3 | H | 1 | 1 | Si(Me)3 |
| 377 | 2-Naphthyl | H | Si(Me)3 | Si(Me)3 | 0 | 0 | Si(Me)3 |
| 378 | 2-Naphthyl | H | Si(Me)3 | Si(Me)3 | 0 | 1 | Si(Me)3 |
| 379 | 2-Naphthyl | H | Si(Me)3 | Si(Me)3 | 1 | 0 | Si(Me)3 |
| 380 | 2-Naphthyl | H | Si(Me)3 | Si(Me)3 | 1 | 1 | Si(Me)3 |
| 381 | 2-Naphthyl | H | Si(Me)3 | Methyl | 0 | 0 | Si(Me)3 |
| 382 | 2-Naphthyl | H | Si(Me)3 | Methyl | 0 | 1 | Si(Me)3 |
| 383 | 2-Naphthyl | H | Si(Me)3 | Methyl | 1 | 0 | Si(Me)3 |
| 384 | 2-Naphthyl | H | Si(Me)3 | Methyl | 1 | 1 | Si(Me)3 |
| 385 | 2-Naphthyl | H | Si(Me)3 | F | 0 | 0 | Si(Me)3 |
| 386 | 2-Naphthyl | H | Si(Me)3 | F | 0 | 1 | Si(Me)3 |
| 387 | 2-Naphthyl | H | Si(Me)3 | F | 1 | 0 | Si(Me)3 |
| 388 | 2-Naphthyl | H | Si(Me)3 | F | 1 | 1 | Si(Me)3 |
| 389 | 2-Naphthyl | H | Si(Me)3 | Phenyl | 0 | 0 | Si(Me)3 |
| 390 | 2-Naphthyl | H | Si(Me)3 | Phenyl | 0 | 1 | Si(Me)3 |
| 391 | 2-Naphthyl | H | Si(Me)3 | Phenyl | 1 | 0 | Si(Me)3 |
| 392 | 2-Naphthyl | H | Si(Me)3 | Phenyl | 1 | 1 | Si(Me)3 |
| 393 | 2-Naphthyl | Si(Me)3 | H | H | 0 | 0 | Si(Me)3 |
| 394 | 2-Naphthyl | Si(Me)3 | H | H | 0 | 1 | Si(Me)3 |
| 395 | 2-Naphthyl | Si(Me)3 | H | H | 1 | 0 | Si(Me)3 |
| 396 | 2-Naphthyl | Si(Me)3 | H | H | 1 | 1 | Si(Me)3 |
| 397 | 2-Naphthyl | Si(Me)3 | H | Si(Me)3 | 0 | 0 | Si(Me)3 |
| 398 | 2-Naphthyl | Si(Me)3 | H | Si(Me)3 | 0 | 1 | Si(Me)3 |
| 399 | 2-Naphthyl | Si(Me)3 | H | Si(Me)3 | 1 | 0 | Si(Me)3 |
| 400 | 2-Naphthyl | Si(Me)3 | H | Si(Me)3 | 1 | 1 | Si(Me)3 |
| 401 | 2-Naphthyl | Si(Me)3 | H | Methyl | 0 | 0 | Si(Me)3 |
| 402 | 2-Naphthyl | Si(Me)3 | H | Methyl | 0 | 1 | Si(Me)3 |
| 403 | 2-Naphthyl | Si(Me)3 | H | Methyl | 1 | 0 | Si(Me)3 |
| 404 | 2-Naphthyl | Si(Me)3 | H | Methyl | 1 | 1 | Si(Me)3 |
| 405 | 2-Naphthyl | Si(Me)3 | H | F | 0 | 0 | Si(Me)3 |
| 406 | 2-Naphthyl | Si(Me)3 | H | F | 0 | 1 | Si(Me)3 |
| 407 | 2-Naphthyl | Si(Me)3 | H | F | 1 | 0 | Si(Me)3 |
| 408 | 2-Naphthyl | Si(Me)3 | H | F | 1 | 1 | Si(Me)3 |
| 409 | 2-Naphthyl | Si(Me)3 | H | Phenyl | 0 | 0 | Si(Me)3 |
| 410 | 2-Naphthyl | Si(Me)3 | H | Phenyl | 0 | 1 | Si(Me)3 |
| 411 | 2-Naphthyl | Si(Me)3 | H | Phenyl | 1 | 0 | Si(Me)3 |
| 412 | 2-Naphthyl | Si(Me)3 | H | Phenyl | 1 | 1 | Si(Me)3 |
| 413 | 2-Naphthyl | Si(Me)3 | Si(Me)3 | H | 0 | 0 | Si(Me)3 |
| 414 | 2-Naphthyl | Si(Me)3 | Si(Me)3 | H | 0 | 1 | Si(Me)3 |
| 415 | 2-Naphthyl | Si(Me)3 | Si(Me)3 | H | 1 | 0 | Si(Me)3 |
| 416 | 2-Naphthyl | Si(Me)3 | Si(Me)3 | H | 1 | 1 | Si(Me)3 |
| 417 | 2-Naphthyl | Si(Me)3 | Si(Me)3 | Si(Me)3 | 0 | 0 | Si(Me)3 |
| 418 | 2-Naphthyl | Si(Me)3 | Si(Me)3 | Si(Me)3 | 0 | 1 | Si(Me)3 |
| 419 | 2-Naphthyl | Si(Me)3 | Si(Me)3 | Si(Me)3 | 1 | 0 | Si(Me)3 |
| 420 | 2-Naphthyl | Si(Me)3 | Si(Me)3 | Si(Me)3 | 1 | 1 | Si(Me)3 |
| 421 | 2-Naphthyl | Si(Me)3 | Si(Me)3 | Methyl | 0 | 0 | Si(Me)3 |
| 422 | 2-Naphthyl | Si(Me)3 | Si(Me)3 | Methyl | 0 | 1 | Si(Me)3 |
| 423 | 2-Naphthyl | Si(Me)3 | Si(Me)3 | Methyl | 1 | 0 | Si(Me)3 |
| 424 | 2-Naphthyl | Si(Me)3 | Si(Me)3 | Methyl | 1 | 1 | Si(Me)3 |
| 425 | 2-Naphthyl | Si(Me)3 | Si(Me)3 | F | 0 | 0 | Si(Me)3 |
| 426 | 2-Naphthyl | Si(Me)3 | Si(Me)3 | F | 0 | 1 | Si(Me)3 |
| 427 | 2-Naphthyl | Si(Me)3 | Si(Me)3 | F | 1 | 0 | Si(Me)3 |
| 428 | 2-Naphthyl | Si(Me)3 | Si(Me)3 | F | 1 | 1 | Si(Me)3 |
| 429 | -Naphthyl | Si(Me)3 | Si(Me)3 | Phenyl | 0 | 0 | Si(Me)3 |
| 430 | 2-Naphthyl | Si(Me)3 | Si(Me)3 | Phenyl | 0 | 1 | Si(Me)3 |
| 431 | 2-Naphthyl | Si(Me)3 | Si(Me)3 | Phenyl | 1 | 0 | Si(Me)3 |
| 432 | 2-Naphthyl | Si(Me)3 | Si(Me)3 | Phenyl | 1 | 1 | Si(Me)3 |
| 433 | para-Tolyl | H | H | Si(Me)3 | 0 | 0 | — |
| 434 | para-Tolyl | H | H | Si(Me)3 | 0 | 1 | — |
| 435 | para-Tolyl | H | H | Si(Me)3 | 1 | 0 | — |
| 436 | para-Tolyl | H | H | Si(Me)3 | 1 | 1 | — |
| 437 | para-Tolyl | H | Si(Me)3 | H | 0 | 0 | — |
| 438 | para-Tolyl | H | Si(Me)3 | H | 0 | 1 | — |
| 439 | para-Tolyl | H | Si(Me)3 | H | 1 | 0 | — |
| 440 | para-Tolyl | H | Si(Me)3 | H | 1 | 1 | — |
| 441 | para-Tolyl | H | Si(Me)3 | Si(Me)3 | 0 | 0 | — |
| 442 | para-Tolyl | H | Si(Me)3 | Si(Me)3 | 0 | 1 | — |
| 443 | para-Tolyl | H | Si(Me)3 | Si(Me)3 | 1 | 0 | — |
| 444 | para-Tolyl | H | Si(Me)3 | Si(Me)3 | 1 | 1 | — |
| 445 | para-Tolyl | H | Si(Me)3 | Methyl | 0 | 0 | — |
| 446 | para-Tolyl | H | Si(Me)3 | Methyl | 0 | 1 | — |
| 447 | para-Tolyl | H | Si(Me)3 | Methyl | 1 | 0 | — |
| 448 | para-Tolyl | H | Si(Me)3 | Methyl | 1 | 1 | — |
| 449 | para-Tolyl | H | Si(Me)3 | F | 0 | 0 | — |
| 450 | para-Tolyl | H | Si(Me)3 | F | 0 | 1 | — |
| 451 | para-Tolyl | H | Si(Me)3 | F | 1 | 0 | — |
| 452 | para-Tolyl | H | Si(Me)3 | F | 1 | 1 | — |
| 453 | para-Tolyl | H | Si(Me)3 | Phenyl | 0 | 0 | — |
| 454 | para-Tolyl | H | Si(Me)3 | Phenyl | 0 | 1 | — |
| 455 | para-Tolyl | H | Si(Me)3 | Phenyl | 1 | 0 | — |
| 456 | para-Tolyl | H | Si(Me)3 | Phenyl | 1 | 1 | — |
| 457 | para-Tolyl | Si(Me)3 | H | H | 0 | 0 | — |
| 458 | para-Tolyl | Si(Me)3 | H | H | 0 | 1 | — |
| 459 | para-Tolyl | Si(Me)3 | H | H | 1 | 0 | — |
| 460 | para-Tolyl | Si(Me)3 | H | H | 1 | 1 | — |
| 461 | para-Tolyl | Si(Me)3 | H | Si(Me)3 | 0 | 0 | — |
| 462 | para-Tolyl | Si(Me)3 | H | Si(Me)3 | 0 | 1 | — |
| 463 | para-Tolyl | Si(Me)3 | H | Si(Me)3 | 1 | 0 | — |
| 464 | para-Tolyl | Si(Me)3 | H | Si(Me)3 | 1 | 1 | — |
| 465 | para-Tolyl | Si(Me)3 | H | Methyl | 0 | 0 | — |
| 466 | para-Tolyl | Si(Me)3 | H | Methyl | 0 | 1 | — |
| 467 | para-Tolyl | Si(Me)3 | H | Methyl | 1 | 0 | — |
| 468 | para-Tolyl | Si(Me)3 | H | Methyl | 1 | 1 | — |

TABLE 1-continued

Preferred structures of the formula (3)

| No. | R | Ra | Rb | Rc | d | m | R' |
|---|---|---|---|---|---|---|---|
| 469 | para-Tolyl | Si(Me)3 | H | F | 0 | 0 | — |
| 470 | para-Tolyl | Si(Me)3 | H | F | 0 | 1 | — |
| 471 | para-Tolyl | Si(Me)3 | H | F | 1 | 0 | — |
| 472 | para-Tolyl | Si(Me)3 | H | F | 1 | 1 | — |
| 473 | para-Tolyl | Si(Me)3 | H | Phenyl | 0 | 0 | — |
| 474 | para-Tolyl | Si(Me)3 | H | Phenyl | 0 | 1 | — |
| 475 | para-Tolyl | Si(Me)3 | H | Phenyl | 1 | 0 | — |
| 476 | para-Tolyl | Si(Me)3 | H | Phenyl | 1 | 1 | — |
| 477 | para-Tolyl | Si(Me)3 | Si(Me)3 | H | 0 | 0 | — |
| 478 | para-Tolyl | Si(Me)3 | Si(Me)3 | H | 0 | 1 | — |
| 479 | para-Tolyl | Si(Me)3 | Si(Me)3 | H | 1 | 0 | — |
| 480 | para-Tolyl | Si(Me)3 | Si(Me)3 | H | 1 | 1 | — |
| 481 | para-Tolyl | Si(Me)3 | Si(Me)3 | Si(Me)3 | 0 | 0 | — |
| 482 | para-Tolyl | Si(Me)3 | Si(Me)3 | Si(Me)3 | 0 | 1 | — |
| 483 | para-Tolyl | Si(Me)3 | Si(Me)3 | Si(Me)3 | 1 | 0 | — |
| 484 | para-Tolyl | Si(Me)3 | Si(Me)3 | Si(Me)3 | 1 | 1 | — |
| 485 | para-Tolyl | Si(Me)3 | Si(Me)3 | Methyl | 0 | 0 | — |
| 486 | para-Tolyl | Si(Me)3 | Si(Me)3 | Methyl | 0 | 1 | — |
| 487 | para-Tolyl | Si(Me)3 | Si(Me)3 | Methyl | 1 | 0 | — |
| 488 | para-Tolyl | Si(Me)3 | Si(Me)3 | Methyl | 1 | 1 | — |
| 489 | para-Tolyl | Si(Me)3 | Si(Me)3 | F | 0 | 0 | — |
| 490 | para-Tolyl | Si(Me)3 | Si(Me)3 | F | 0 | 1 | — |
| 491 | para-Tolyl | Si(Me)3 | Si(Me)3 | F | 1 | 0 | — |
| 492 | para-Tolyl | Si(Me)3 | Si(Me)3 | F | 1 | 1 | — |
| 493 | para-Tolyl | Si(Me)3 | Si(Me)3 | Phenyl | 0 | 0 | — |
| 494 | para-Tolyl | Si(Me)3 | Si(Me)3 | Phenyl | 0 | 1 | — |
| 495 | para-Tolyl | Si(Me)3 | Si(Me)3 | Phenyl | 1 | 0 | — |
| 496 | para-Tolyl | Si(Me)3 | Si(Me)3 | Phenyl | 1 | 1 | — |
| 497 | 2-Biphenyl | H | H | Si(Me)3 | 0 | 0 | — |
| 498 | 2-Biphenyl | H | H | Si(Me)3 | 0 | 1 | — |
| 499 | 2-Biphenyl | H | H | Si(Me)3 | 1 | 0 | — |
| 500 | 2-Biphenyl | H | H | Si(Me)3 | 1 | 1 | — |
| 501 | 2-Biphenyl | H | Si(Me)3 | H | 0 | 0 | — |
| 502 | 2-Biphenyl | H | Si(Me)3 | H | 0 | 1 | — |
| 503 | 2-Biphenyl | H | Si(Me)3 | H | 1 | 0 | — |
| 504 | 2-Biphenyl | H | Si(Me)3 | H | 1 | 1 | — |
| 505 | 2-Biphenyl | H | Si(Me)3 | Si(Me)3 | 0 | 0 | — |
| 506 | 2-Biphenyl | H | Si(Me)3 | Si(Me)3 | 0 | 1 | — |
| 507 | 2-Biphenyl | H | Si(Me)3 | Si(Me)3 | 1 | 0 | — |
| 508 | 2-Biphenyl | H | Si(Me)3 | Si(Me)3 | 1 | 1 | — |
| 509 | 2-Biphenyl | H | Si(Me)3 | Methyl | 0 | 0 | — |
| 510 | 2-Biphenyl | H | Si(Me)3 | Methyl | 0 | 1 | — |
| 511 | 2-iphenyl | H | Si(Me)3 | Methyl | 1 | 0 | — |
| 512 | 2-Biphenyl | H | Si(Me)3 | Methyl | 1 | 1 | — |
| 513 | 2-Biphenyl | H | Si(Me)3 | F | 0 | 0 | — |
| 514 | 2-Biphenyl | H | Si(Me)3 | F | 0 | 1 | — |
| 515 | 2-Biphenyl | H | Si(Me)3 | F | 1 | 0 | — |
| 516 | 2-Biphenyl | H | Si(Me)3 | F | 1 | 1 | — |
| 517 | 2-Biphenyl | H | Si(Me)3 | Phenyl | 0 | 0 | — |
| 518 | 2-Biphenyl | H | Si(Me)3 | Phenyl | 0 | 1 | — |
| 519 | 2-Biphenyl | H | Si(Me)3 | Phenyl | 1 | 0 | — |
| 520 | 2-Biphenyl | H | Si(Me)3 | Phenyl | 1 | 1 | — |
| 521 | 2-Biphenyl | Si(Me)3 | H | H | 0 | 0 | — |
| 522 | 2-Biphenyl | Si(Me)3 | H | H | 0 | 1 | — |
| 523 | 2-Biphenyl | Si(Me)3 | H | H | 1 | 0 | — |
| 524 | 2-Biphenyl | Si(Me)3 | H | H | 1 | 1 | — |
| 525 | 2-Biphenyl | Si(Me)3 | H | Si(Me)3 | 0 | 0 | — |
| 526 | 2-Biphenyl | Si(Me)3 | H | Si(Me)3 | 0 | 1 | — |
| 527 | 2-Biphenyl | Si(Me)3 | H | Si(Me)3 | 1 | 0 | — |
| 528 | 2-Biphenyl | Si(Me)3 | H | Si(Me)3 | 1 | 1 | — |
| 529 | 2-Biphenyl | Si(Me)3 | H | Methyl | 0 | 0 | — |
| 530 | 2-Biphenyl | Si(Me)3 | H | Methyl | 0 | 1 | — |
| 531 | 2-Biphenyl | Si(Me)3 | H | Methyl | 1 | 0 | — |
| 532 | 2-Biphenyl | Si(Me)3 | H | Methyl | 1 | 1 | — |
| 533 | 2-Biphenyl | Si(Me)3 | H | F | 0 | 0 | — |
| 534 | 2-Biphenyl | Si(Me)3 | H | F | 0 | 1 | — |
| 535 | 2-Biphenyl | Si(Me)3 | H | F | 1 | 0 | — |
| 536 | 2-Biphenyl | Si(Me)3 | H | F | 1 | 1 | — |
| 537 | 2-Biphenyl | Si(Me)3 | H | Phenyl | 0 | 0 | — |
| 538 | 2-Biphenyl | Si(Me)3 | H | Phenyl | 0 | 1 | — |
| 539 | 2-Biphenyl | Si(Me)3 | H | Phenyl | 1 | 0 | — |
| 540 | 2-Biphenyl | Si(Me)3 | H | Phenyl | 1 | 1 | — |
| 541 | 2-Biphenyl | Si(Me)3 | Si(Me)3 | H | 0 | 0 | — |
| 542 | 2-Biphenyl | Si(Me)3 | Si(Me)3 | H | 0 | 1 | — |
| 543 | 2-Biphenyl | Si(Me)3 | Si(Me)3 | H | 1 | 0 | — |
| 544 | 2-Biphenyl | Si(Me)3 | Si(Me)3 | H | 1 | 1 | — |
| 545 | 2-Biphenyl | Si(Me)3 | Si(Me)3 | Si(Me)3 | 0 | 0 | — |
| 546 | 2-Biphenyl | Si(Me)3 | Si(Me)3 | Si(Me)3 | 0 | 1 | — |
| 547 | 2-Biphenyl | Si(Me)3 | Si(Me)3 | Si(Me)3 | 1 | 0 | — |
| 548 | 2-Biphenyl | Si(Me)3 | Si(Me)3 | Si(Me)3 | 1 | 1 | — |
| 549 | 2-Biphenyl | Si(Me)3 | Si(Me)3 | Methyl | 0 | 0 | — |
| 550 | 2-Biphenyl | Si(Me)3 | Si(Me)3 | Methyl | 0 | 1 | — |
| 551 | 2-Biphenyl | Si(Me)3 | Si(Me)3 | Methyl | 1 | 0 | — |
| 552 | 2-Biphenyl | Si(Me)3 | Si(Me)3 | Methyl | 1 | 1 | — |
| 553 | 2-Biphenyl | Si(Me)3 | Si(Me)3 | F | 0 | 0 | — |
| 554 | 2-Biphenyl | Si(Me)3 | Si(Me)3 | F | 0 | 1 | — |
| 555 | 2-Biphenyl | Si(Me)3 | Si(Me)3 | F | 1 | 0 | — |
| 556 | 2-Biphenyl | Si(Me)3 | Si(Me)3 | F | 1 | 1 | — |
| 557 | 2-Biphenyl | Si(Me)3 | Si(Me)3 | Phenyl | 0 | 0 | — |
| 558 | 2-Biphenyl | Si(Me)3 | Si(Me)3 | Phenyl | 0 | 1 | — |
| 559 | 2-Biphenyl | Si(Me)3 | Si(Me)3 | Phenyl | 1 | 0 | — |
| 560 | 2-Biphenyl | Si(Me)3 | Si(Me)3 | Phenyl | 1 | 1 | — |
| 561 | N(Ph)2 | H | H | Si(Me)3 | 0 | 0 | — |
| 562 | N(Ph)2 | H | H | Si(Me)3 | 0 | 1 | — |
| 563 | N(Ph)2 | H | H | Si(Me)3 | 1 | 0 | — |
| 564 | N(Ph)2 | H | H | Si(Me)3 | 1 | 1 | — |
| 565 | N(Ph)2 | H | Si(Me)3 | H | 0 | 0 | — |
| 566 | N(Ph)2 | H | Si(Me)3 | H | 0 | 1 | — |
| 567 | N(Ph)2 | H | Si(Me)3 | H | 1 | 0 | — |
| 568 | N(Ph)2 | H | Si(Me)3 | H | 1 | 1 | — |
| 569 | N(Ph)2 | H | Si(Me)3 | Si(Me)3 | 0 | 0 | — |
| 570 | N(Ph)2 | H | Si(Me)3 | Si(Me)3 | 0 | 1 | — |
| 571 | N(Ph)2 | H | Si(Me)3 | Si(Me)3 | 1 | 0 | — |
| 572 | N(Ph)2 | H | Si(Me)3 | Si(Me)3 | 1 | 1 | — |
| 573 | N(Ph)2 | H | Si(Me)3 | Methyl | 0 | 0 | — |
| 574 | N(Ph)2 | H | Si(Me)3 | Methyl | 0 | 1 | — |
| 575 | N(Ph)2 | H | Si(Me)3 | Methyl | 1 | 0 | — |
| 576 | N(Ph)2 | H | Si(Me)3 | Methyl | 1 | 1 | — |
| 577 | N(Ph)2 | H | Si(Me)3 | F | 0 | 0 | — |
| 578 | N(Ph)2 | H | Si(Me)3 | F | 0 | 1 | — |
| 579 | N(Ph)2 | H | Si(Me)3 | F | 1 | 0 | — |
| 580 | N(Ph)2 | H | Si(Me)3 | F | 1 | 1 | — |
| 581 | N(Ph)2 | H | Si(Me)3 | Phenyl | 0 | 0 | — |
| 582 | N(Ph)2 | H | Si(Me)3 | Phenyl | 0 | 1 | — |
| 583 | N(Ph)2 | H | Si(Me)3 | Phenyl | 1 | 0 | — |
| 584 | N(Ph)2 | H | Si(Me)3 | Phenyl | 1 | 1 | — |
| 585 | N(Ph)2 | Si(Me)3 | H | H | 0 | 0 | — |
| 586 | N(Ph)2 | Si(Me)3 | H | H | 0 | 1 | — |
| 587 | N(Ph)2 | Si(Me)3 | H | H | 1 | 0 | — |
| 588 | N(Ph)2 | Si(Me)3 | H | H | 1 | 1 | — |
| 589 | N(Ph)2 | Si(Me)3 | H | Si(Me)3 | 0 | 0 | — |
| 590 | N(Ph)2 | Si(Me)3 | H | Si(Me)3 | 0 | 1 | — |
| 591 | N(Ph)2 | Si(Me)3 | H | Si(Me)3 | 1 | 0 | — |
| 592 | N(Ph)2 | Si(Me)3 | H | Si(Me)3 | 1 | 1 | — |
| 593 | N(Ph)2 | Si(Me)3 | H | Methyl | 0 | 0 | — |
| 594 | N(Ph)2 | Si(Me)3 | H | Methyl | 0 | 1 | — |
| 595 | N(Ph)2 | Si(Me)3 | H | Methyl | 1 | 0 | — |
| 596 | N(Ph)2 | Si(Me)3 | H | Methyl | 1 | 1 | — |
| 597 | N(Ph)2 | Si(Me)3 | H | F | 0 | 0 | — |
| 598 | N(Ph)2 | Si(Me)3 | H | F | 0 | 1 | — |
| 599 | N(Ph)2 | Si(Me)3 | H | F | 1 | 0 | — |
| 600 | N(Ph)2 | Si(Me)3 | H | F | 1 | 1 | — |
| 601 | N(Ph)2 | Si(Me)3 | H | Phenyl | 0 | 0 | — |
| 602 | N(Ph)2 | Si(Me)3 | H | Phenyl | 0 | 1 | — |
| 603 | N(Ph)2 | Si(Me)3 | H | Phenyl | 1 | 0 | — |
| 604 | N(Ph)2 | Si(Me)3 | H | Phenyl | 1 | 1 | — |
| 605 | N(Ph)2 | Si(Me)3 | Si(Me)3 | H | 0 | 0 | — |
| 606 | N(Ph)2 | Si(Me)3 | Si(Me)3 | H | 0 | 1 | — |
| 607 | N(Ph)2 | Si(Me)3 | Si(Me)3 | H | 1 | 0 | — |
| 608 | N(Ph)2 | Si(Me)3 | Si(Me)3 | H | 1 | 1 | — |
| 609 | N(Ph)2 | Si(Me)3 | Si(Me)3 | Si(Me)3 | 0 | 0 | — |
| 610 | N(Ph)2 | Si(Me)3 | Si(Me)3 | Si(Me)3 | 0 | 1 | — |
| 611 | N(Ph)2 | Si(Me)3 | Si(Me)3 | Si(Me)3 | 1 | 0 | — |
| 612 | N(Ph)2 | Si(Me)3 | Si(Me)3 | Si(Me)3 | 1 | 1 | — |
| 613 | N(Ph)2 | Si(Me)3 | Si(Me)3 | Methyl | 0 | 0 | — |
| 614 | N(Ph)2 | Si(Me)3 | Si(Me)3 | Methyl | 0 | 1 | — |
| 615 | N(Ph)2 | Si(Me)3 | Si(Me)3 | Methyl | 1 | 0 | — |
| 616 | N(Ph)2 | Si(Me)3 | Si(Me)3 | Methyl | 1 | 1 | — |
| 617 | N(Ph)2 | Si(Me)3 | Si(Me)3 | F | 0 | 0 | — |
| 618 | N(Ph)2 | Si(Me)3 | Si(Me)3 | F | 0 | 1 | — |
| 619 | N(Ph)2 | Si(Me)3 | Si(Me)3 | F | 1 | 0 | — |
| 620 | N(Ph)2 | Si(Me)3 | Si(Me)3 | F | 1 | 1 | — |

TABLE 1-continued

Preferred structures of the formula (3)

| No. | R | Ra | Rb | Rc | d | m | R' |
|---|---|---|---|---|---|---|---|
| 621 | N(Ph)2 | Si(Me)3 | Si(Me)3 | Phenyl | 0 | 0 | — |
| 622 | N(Ph)2 | Si(Me)3 | Si(Me)3 | Phenyl | 0 | 1 | — |
| 623 | N(Ph)2 | Si(Me)3 | Si(Me)3 | Phenyl | 1 | 0 | — |
| 624 | N(Ph)2 | Si(Me)3 | Si(Me)3 | Phenyl | 1 | 1 | — |
| 625 | N(p-Tol)2 | H | H | Si(Me)3 | 0 | 0 | — |
| 626 | N(p-Tol)2 | H | H | Si(Me)3 | 0 | 1 | — |
| 627 | N(p-Tol)2 | H | H | Si(Me)3 | 1 | 0 | — |
| 628 | N(p-Tol)2 | H | H | Si(Me)3 | 1 | 1 | — |
| 629 | N(p-Tol)2 | H | Si(Me)3 | H | 0 | 0 | — |
| 630 | N(p-Tol)2 | H | Si(Me)3 | H | 0 | 1 | — |
| 631 | N(p-Tol)2 | H | Si(Me)3 | H | 1 | 0 | — |
| 632 | N(p-Tol)2 | H | Si(Me)3 | H | 1 | 1 | — |
| 633 | N(p-Tol)2 | H | Si(Me)3 | Si(Me)3 | 0 | 0 | — |
| 634 | N(p-Tol)2 | H | Si(Me)3 | Si(Me)3 | 0 | 1 | — |
| 635 | N(p-Tol)2 | H | Si(Me)3 | Si(Me)3 | 1 | 0 | — |
| 636 | N(p-Tol)2 | H | Si(Me)3 | Si(Me)3 | 1 | 1 | — |
| 637 | N(p-Tol)2 | H | Si(Me)3 | Methyl | 0 | 0 | — |
| 638 | N(p-Tol)2 | H | Si(Me)3 | Methyl | 0 | 1 | — |
| 639 | N(p-Tol)2 | H | Si(Me)3 | Methyl | 1 | 0 | — |
| 640 | N(p-Tol)2 | H | Si(Me)3 | Methyl | 1 | 1 | — |
| 641 | N(p-Tol)2 | H | Si(Me)3 | F | 0 | 0 | — |
| 642 | N(p-Tol)2 | H | Si(Me)3 | F | 0 | 1 | — |
| 643 | N(p-Tol)2 | H | Si(Me)3 | F | 1 | 0 | — |
| 644 | N(p-Tol)2 | H | Si(Me)3 | F | 1 | 1 | — |
| 645 | N(p-Tol)2 | H | Si(Me)3 | Phenyl | 0 | 0 | — |
| 646 | N(p-Tol)2 | H | Si(Me)3 | Phenyl | 0 | 1 | — |
| 647 | N(p-Tol)2 | H | Si(Me)3 | Phenyl | 1 | 0 | — |
| 648 | N(p-Tol)2 | H | Si(Me)3 | Phenyl | 1 | 1 | — |
| 649 | N(p-Tol)2 | Si(Me)3 | H | H | 0 | 0 | — |
| 650 | N(p-Tol)2 | Si(Me)3 | H | H | 0 | 1 | — |
| 651 | N(p-Tol)2 | Si(Me)3 | H | H | 1 | 0 | — |
| 652 | N(p-Tol)2 | Si(Me)3 | H | H | 1 | 1 | — |
| 653 | N(p-Tol)2 | Si(Me)3 | H | Si(Me)3 | 0 | 0 | — |
| 654 | N(p-Tol)2 | Si(Me)3 | H | Si(Me)3 | 0 | 1 | — |
| 655 | N(p-Tol)2 | Si(Me)3 | H | Si(Me)3 | 1 | 0 | — |
| 656 | N(p-Tol)2 | Si(Me)3 | H | Si(Me)3 | 1 | 1 | — |
| 657 | N(p-Tol)2 | Si(Me)3 | H | Methyl | 0 | 0 | — |
| 658 | N(p-Tol)2 | Si(Me)3 | H | Methyl | 0 | 1 | — |
| 659 | N(p-Tol)2 | Si(Me)3 | H | Methyl | 1 | 0 | — |
| 660 | N(p-Tol)2 | Si(Me)3 | H | Methyl | 1 | 1 | — |
| 661 | N(p-Tol)2 | Si(Me)3 | H | F | 0 | 0 | — |
| 662 | N(p-Tol)2 | Si(Me)3 | H | F | 0 | 1 | — |
| 663 | N(p-Tol)2 | Si(Me)3 | H | F | 1 | 0 | — |
| 664 | N(p-Tol)2 | Si(Me)3 | H | F | 1 | 1 | — |
| 665 | N(p-Tol)2 | Si(Me)3 | H | Phenyl | 0 | 0 | — |
| 666 | N(p-Tol)2 | Si(Me)3 | H | Phenyl | 0 | 1 | — |
| 667 | N(p-Tol)2 | Si(Me)3 | H | Phenyl | 1 | 0 | — |
| 668 | N(p-Tol)2 | Si(Me)3 | H | Phenyl | 1 | 1 | — |
| 669 | N(p-Tol)2 | Si(Me)3 | Si(Me)3 | H | 0 | 0 | — |
| 670 | N(p-Tol)2 | Si(Me)3 | Si(Me)3 | H | 0 | 1 | — |
| 671 | N(p-Tol)2 | Si(Me)3 | Si(Me)3 | H | 1 | 0 | — |
| 672 | N(p-Tol)2 | Si(Me)3 | Si(Me)3 | H | 1 | 1 | — |
| 673 | N(p-Tol)2 | Si(Me)3 | Si(Me)3 | Si(Me)3 | 0 | 0 | — |
| 674 | N(p-Tol)2 | Si(Me)3 | Si(Me)3 | Si(Me)3 | 0 | 1 | — |
| 675 | N(p-Tol)2 | Si(Me)3 | Si(Me)3 | Si(Me)3 | 1 | 0 | — |
| 676 | N(p-Tol)2 | Si(Me)3 | Si(Me)3 | Si(Me)3 | 1 | 1 | — |
| 677 | N(p-Tol)2 | Si(Me)3 | Si(Me)3 | Methyl | 0 | 0 | — |
| 678 | N(p-Tol)2 | Si(Me)3 | Si(Me)3 | Methyl | 0 | 1 | — |
| 679 | N(p-Tol)2 | Si(Me)3 | Si(Me)3 | Methyl | 1 | 0 | — |
| 680 | N(p-Tol)2 | Si(Me)3 | Si(Me)3 | Methyl | 1 | 1 | — |
| 681 | N(p-Tol)2 | Si(Me)3 | Si(Me)3 | F | 0 | 0 | — |
| 682 | N(p-Tol)2 | Si(Me)3 | Si(Me)3 | F | 0 | 1 | — |
| 683 | N(p-Tol)2 | Si(Me)3 | Si(Me)3 | F | 1 | 0 | — |
| 684 | N(p-Tol)2 | Si(Me)3 | Si(Me)3 | F | 1 | 1 | — |
| 685 | N(p-Tol)2 | Si(Me)3 | Si(Me)3 | Phenyl | 0 | 0 | — |
| 686 | N(p-Tol)2 | Si(Me)3 | Si(Me)3 | Phenyl | 0 | 1 | — |
| 687 | N(p-Tol)2 | Si(Me)3 | Si(Me)3 | Phenyl | 1 | 0 | — |
| 688 | N(p-Tol)2 | Si(Me)3 | Si(Me)3 | Phenyl | 1 | 1 | — |
| 689 | N(Ph)(1-Naph) | H | H | Si(Me)3 | 0 | 0 | — |
| 690 | N(Ph)(1-Naph) | H | H | Si(Me)3 | 0 | 1 | — |
| 691 | N(Ph)(1-Naph) | H | H | Si(Me)3 | 1 | 0 | — |
| 692 | N(Ph)(1-Naph) | H | H | Si(Me)3 | 1 | 1 | — |
| 693 | N(Ph)(1-Naph) | H | Si(Me)3 | H | 0 | 0 | — |
| 694 | N(Ph)(1-Naph) | H | Si(Me)3 | H | 0 | 1 | — |
| 695 | N(Ph)(1-Naph) | H | Si(Me)3 | H | 1 | 0 | — |
| 696 | N(Ph)(1-Naph) | H | Si(Me)3 | H | 1 | 1 | — |
| 697 | N(Ph)(1-Naph) | H | Si(Me)3 | Si(Me)3 | 0 | 0 | — |
| 698 | N(Ph)(1-Naph) | H | Si(Me)3 | Si(Me)3 | 0 | 1 | — |
| 699 | N(Ph)(1-Naph) | H | Si(Me)3 | Si(Me)3 | 1 | 0 | — |
| 700 | N(Ph)(1-Naph) | H | Si(Me)3 | Si(Me)3 | 1 | 1 | — |
| 701 | N(Ph)(1-Naph) | H | Si(Me)3 | Methyl | 0 | 0 | — |
| 702 | N(Ph)(1-Naph) | H | Si(Me)3 | Methyl | 0 | 1 | — |
| 703 | N(Ph)(1-Naph) | H | Si(Me)3 | Methyl | 1 | 0 | — |
| 704 | N(Ph)(1-Naph) | H | Si(Me)3 | Methyl | 1 | 1 | — |
| 705 | N(Ph)(1-Naph) | H | Si(Me)3 | F | 0 | 0 | — |
| 706 | N(Ph)(1-Naph) | H | Si(Me)3 | F | 0 | 1 | — |
| 707 | N(Ph)(1-Naph) | H | Si(Me)3 | F | 1 | 0 | — |
| 708 | N(Ph)(1-Naph) | H | Si(Me)3 | F | 1 | 1 | — |
| 709 | N(Ph)(1-Naph) | H | Si(Me)3 | Phenyl | 0 | 0 | — |
| 710 | N(Ph)(1-Naph) | H | Si(Me)3 | Phenyl | 0 | 1 | — |
| 711 | N(Ph)(1-Naph) | H | Si(Me)3 | Phenyl | 1 | 0 | — |
| 712 | N(Ph)(1-Naph) | H | Si(Me)3 | Phenyl | 1 | 1 | — |
| 713 | N(Ph)(1-Naph) | Si(Me)3 | H | H | 0 | 0 | — |
| 714 | N(Ph)(1-Naph) | Si(Me)3 | H | H | 0 | 1 | — |
| 715 | N(Ph)(1-Naph) | Si(Me)3 | H | H | 1 | 0 | — |
| 716 | N(Ph)(1-Naph) | Si(Me)3 | H | H | 1 | 1 | — |
| 717 | N(Ph)(1-Naph) | Si(Me)3 | H | Si(Me)3 | 0 | 0 | — |
| 718 | N(Ph)(1-Naph) | Si(Me)3 | H | Si(Me)3 | 0 | 1 | — |
| 719 | N(Ph)(1-Naph) | Si(Me)3 | H | Si(Me)3 | 1 | 0 | — |
| 720 | N(Ph)(1-Naph) | Si(Me)3 | H | Si(Me)3 | 1 | 1 | — |
| 721 | N(Ph)(1-Naph) | Si(Me)3 | H | Methyl | 0 | 0 | — |
| 722 | N(Ph)(1-Naph) | Si(Me)3 | H | Methyl | 0 | 1 | — |
| 723 | N(Ph)(1-Naph) | Si(Me)3 | H | Methyl | 1 | 0 | — |
| 724 | N(Ph)(1-Naph) | Si(Me)3 | H | Methyl | 1 | 1 | — |
| 725 | N(Ph)(1-Naph) | Si(Me)3 | H | F | 0 | 0 | — |
| 726 | N(Ph)(1-Naph) | Si(Me)3 | H | F | 0 | 1 | — |
| 727 | N(Ph)(1-Naph) | Si(Me)3 | H | F | 1 | 0 | — |
| 728 | N(Ph)(1-Naph) | Si(Me)3 | H | F | 1 | 1 | — |
| 729 | N(Ph)(1-Naph) | Si(Me)3 | H | Phenyl | 0 | 0 | — |
| 730 | N(Ph)(1-Naph) | Si(Me)3 | H | Phenyl | 0 | 1 | — |
| 731 | N(Ph)(1-Naph) | Si(Me)3 | H | Phenyl | 1 | 0 | — |
| 732 | N(Ph)(1-Naph) | Si(Me)3 | H | Phenyl | 1 | 1 | — |
| 733 | N(Ph)(1-Naph) | Si(Me)3 | Si(Me)3 | H | 0 | 0 | — |
| 734 | N(Ph)(1-Naph) | Si(Me)3 | Si(Me)3 | H | 0 | 1 | — |
| 735 | N(Ph)(1-Naph) | Si(Me)3 | Si(Me)3 | H | 1 | 0 | — |
| 736 | N(Ph)(1-Naph) | Si(Me)3 | Si(Me)3 | H | 1 | 1 | — |
| 737 | N(Ph)(1-Naph) | Si(Me)3 | Si(Me)3 | Si(Me)3 | 0 | 0 | — |
| 738 | N(Ph)(1-Naph) | Si(Me)3 | Si(Me)3 | Si(Me)3 | 0 | 1 | — |
| 739 | N(Ph)(1-Naph) | Si(Me)3 | Si(Me)3 | Si(Me)3 | 1 | 0 | — |
| 740 | N(Ph)(1-Naph) | Si(Me)3 | Si(Me)3 | Si(Me)3 | 1 | 1 | — |
| 741 | N(Ph)(1-Naph) | Si(Me)3 | Si(Me)3 | Methyl | 0 | 0 | — |
| 742 | N(Ph)(1-Naph) | Si(Me)3 | Si(Me)3 | Methyl | 0 | 1 | — |
| 743 | N(Ph)(1-Naph) | Si(Me)3 | Si(Me)3 | Methyl | 1 | 0 | — |
| 744 | N(Ph)(1-Naph) | Si(Me)3 | Si(Me)3 | Methyl | 1 | 1 | — |
| 745 | N(Ph)(1-Naph) | Si(Me)3 | Si(Me)3 | F | 0 | 0 | — |
| 746 | N(Ph)(1-Naph) | Si(Me)3 | Si(Me)3 | F | 0 | 1 | — |
| 747 | N(Ph)(1-Naph) | Si(Me)3 | Si(Me)3 | F | 1 | 0 | — |
| 748 | N(Ph)(1-Naph) | Si(Me)3 | Si(Me)3 | F | 1 | 1 | — |
| 749 | N(Ph)(1-Naph) | Si(Me)3 | Si(Me)3 | Phenyl | 0 | 0 | — |
| 750 | N(Ph)(1-Naph) | Si(Me)3 | Si(Me)3 | Phenyl | 0 | 1 | — |
| 751 | N(Ph)(1-Naph) | Si(Me)3 | Si(Me)3 | Phenyl | 1 | 0 | — |
| 752 | N(Ph)(1-Naph) | Si(Me)3 | Si(Me)3 | Phenyl | 1 | 1 | — |

The compounds of the formula (1) can be employed in organic electroluminescent devices. Depending on the substitution pattern, they are suitable for use as host material, in particular for fluorescent emitters, as emitter, as hole-transport material, as hole-blocking material and/or as electron-transport material.

The invention therefore furthermore relates to the use of compounds of the formula (1) in organic electronic devices, in particular in organic electroluminescent devices, in particular as host material, as emitter, as hole-transport material, as hole-blocking material and/or as electron-transport material.

The invention furthermore relates to organic electronic devices, in particular organic electroluminescent devices, comprising anode, cathode and at least one emitting layer, where at least one layer comprises at least one compound of the formula (1). The layer comprising the compound of the formula (1) is preferably an emitting layer, a hole-transport layer, a hole-injection layer, a hole-blocking layer or an electron-transport layer.

Besides the cathode, anode and emitting layer (or emitting layers), the organic electroluminescent device may also comprise further layers. These can be, for example: hole-injection layer, hole-transport layer, hole-blocking layer, electron-transport layer, electron-injection layer and/or charge-generation layer (T. Matsumoto et al., *Multiphoton Organic EL Device Having Charge Generation Layer*, IDMC 2003, Taiwan; Session 21 OLED (5)). The materials in these layers may also be doped. Each of these layers does not necessarily have to be present. Suitable hole-transport materials are, for example, aromatic amines, as usually used in accordance with the prior art, which may also be p-doped. Suitable electron-transport materials are, for example, metal-chelate complexes, for example $AlQ_3$, compounds based on electron-deficient heterocycles, for example triazine derivatives, or compounds containing aromatic carbonyls or phosphine oxides, as described, for example, in WO 05/084081 and WO 05/084082, each of which may also be n-doped. Suitable electron-injection materials are, in particular, fluorides and oxides of the alkali metals and alkaline earth metals, for example NaF, $BaF_2$, $CaF_2$, LiF or $Li_2O$.

If the symbol R stands for an aromatic or heteroaromatic ring system, in particular for a condensed aryl or heteroaryl group, the compound of the formula (1) is particularly suitable as host material, in particular for fluorescent emitters, and/or as electron-transport material and/or as hole-blocking material.

A host material is taken to mean the component in a system comprising host and dopant which is present in the greater proportion in the system. In a system comprising a host and a plurality of dopants, the host is taken to mean the component whose proportion is the greatest in the mixture.

The proportion of the host material of the formula (1) in the emitting layer is between 50.0 and 99.9% by weight, preferably between 80.0 and 99.5% by weight, particularly preferably between 90.0 and 99.0% by weight. Correspondingly, the proportion of the dopant in the emitting layer is between 0.1 and 50.0% by weight, preferably between 0.5 and 20.0% by weight, particularly preferably between 1.0 and 10.0% by weight.

Preferred dopants are selected from the class of the aromatic anthracenamines, the aromatic anthracenediamines, the aromatic pyrenamines, the aromatic pyrenediamines, the aromatic chrysenamines, the aromatic chrysenediamines, the monostyrylamines, the distyrylamines, the tristyrylamines, the tetrastyrylamines, the styrylphosphines, the styryl ethers and the arylamines. An aromatic anthracenamine is taken to mean a compound in which a diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines and pyrenediamines or aromatic chrysenamines and chrysenediamines are defined analogously thereto. A monostyrylamine is taken to mean a compound which contains a styryl group and at least one, preferably aromatic amine. A distyrylamine is taken to mean a compound which contains two styryl groups and at least one, preferably aromatic amine. A tristyrylamine is taken to mean a compound which contains three styryl groups and at least one, preferably aromatic amine. A tetrastyrylamine is taken to mean a compound which contains four styryl groups and at least one, preferably aromatic amine. Corresponding phosphines and ethers are defined analogously to the amines. For the purposes of this invention, an arylamine or an aromatic amine is taken to mean a compound which contains three aromatic or heteroaromatic ring systems bonded directly to the nitrogen. The styryl groups are particularly preferably stilbenes, which may also be further substituted. Particularly preferred dopants are selected from the classes of the tristilbenamines, the aromatic stilbenediamines, the anthracenediamines and the pyrenediamines. Very particularly preferred dopants are selected from the class of the tristyrylamines. Examples of dopants of this type are substituted or unsubstituted tristilbenamines or the dopants described in WO 06/000388, WO 06/058737 and WO 06/000389.

Preference is furthermore given to organic electroluminescent devices, characterised in that a plurality of emitting layers are used, where at least one of these layers comprises at least one compound of the formula (1). These emission layers particularly preferably have in total a plurality of emission maxima between 380 nm and 750 nm, resulting overall in white emission, i.e. at least one further emitting compound which is able to fluoresce or phosphoresce and emits yellow, orange or red light is also used in the further emitting layer(s). Particular preference is given to three-layer systems, where at least one of these layers comprises at least one compound of the formula (1) and where the three layers exhibit blue, green and orange or red emission (for the basic structure see, for example, WO 05/011013). Emitters which have broad-band emission bands and thus exhibit white emission are likewise suitable for white emission.

In addition to the compounds of the formula (1), further substances may also be present in the emitting layer, for example hole- or electron-transport materials.

If the symbol R stands for an $N(Ar^1)_2$ group and/or a substituent on the Ar group stands for an $N(Ar^1)_2$ group, the compound of the formula (1) is particularly suitable as emitting compound and/or as hole-transport material, as described in greater detail below.

If the compound of the formula (1) is employed as hole-transport material, it is preferably employed in a hole-transport layer and/or in a hole-injection layer. For the purposes of this invention, a hole-injection layer is a layer which is directly adjacent to the anode. For the purposes of this invention, a hole-transport layer is a layer which lies between a hole-injection layer and an emission layer. If the compounds of the formula (1) are used as hole-transport or hole-injection material, it may be preferred for them to be doped with electron-acceptor compounds, for example with $F_4$-TCNQ or with compounds as described in EP 1476881 or EP 1596445.

If the compound of the formula (1) is employed as emitting compound, it is preferably employed in combination with a host material.

The proportion of the emitting compound of the formula (1) in the mixture of the emitting layer is between 0.1 and 50.0% by weight, preferably between 0.5 and 20.0% by weight, particularly preferably between 1.0 and 10.0% by weight. Correspondingly, the proportion of the host material in the layer is between 50.0 and 99.9% by weight, preferably between 80.0 and 99.5% by weight, particularly preferably between 90.0 and 99.0% by weight.

Suitable host materials are various classes of substance. Preferred host materials are selected from the classes of the oligoarylenes (for example 2, 2',7,7'-tetraphenylspirobifluorene as described in EP 676461 or dinaphthylanthracene), in particular oligoarylenes containing condensed aromatic groups, oligoarylenevinylenes (for example DPVBi or spiro-DPVBi as described in EP 676461), polypodal metal complexes (for example as described in WO 04/081017), hole-conducting compounds (for example as described in WO 04/058911), electron-conducting compounds, in particular ketones, phosphine oxides, sulfoxides, etc. (for example as described in WO 05/084081 or WO 05/084082), atropisomers (for example as described in WO 06/048268) or boronic acid derivatives (for example as described in the unpublished application EP 05009643.7). Particularly preferred host materials are selected from the classes of the oligoarylenes containing naphthalene, anthracene and/or pyrene or atropisomers of these compounds, oligoarylenevinylenes, ketones, phosphine oxides and sulfoxides. Very particularly preferred host materials are selected from the classes of the oligoarylenes containing anthracene and/or pyrene or atropisomers of these compounds, phosphine oxides and sulfoxides.

Preference is furthermore given to an organic electroluminescent device, characterised in that one or more layers are coated by means of a sublimation method, where the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by means of the OVPD (organic vapour phase deposition) method or with the aid of carrier-gas sublimation, where the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermotransfer printing) or ink-jet printing. Soluble compounds of the formula (1) are necessary for this purpose. The compounds according to the invention are therefore very highly suitable for processing from solution since they have high solubility in organic solvents due to the substitution.

The organic electroluminescent devices according to the invention have the following surprising advantages over the prior art:

1. The thermal stability and in particular the glass-transition temperature of the compounds becomes higher compared with compounds in accordance with the prior art which do not contain any trialkylsilyl groups while otherwise having the same structure.
2. The compounds according to the invention have very good solubility in common organic solvents, which simplifies the purification of the compounds during preparation and the cleaning of the vapour-deposition units (for example the shadow masks) and enables the compounds to be applied by solution processes.
3. The compounds according to the invention have higher hole and electron stability (redox stability) compared with comparable materials in accordance with the prior art which do not contain any $Si(R^2)_3$ groups.

The present application text is directed to the use of compounds according to the invention in relation to OLEDs and the corresponding displays.

In spite of this restriction of the description, it is possible for the person skilled in the art, without further inventive step, also to use the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), organic photoreceptors, light-emitting electrochemical cells (LECs) or organic laser diodes (O-lasers).

The present invention furthermore relates to the use of the compounds according to the invention in the corresponding devices and to these devices themselves.

The invention is explained in greater detail by the following examples without wishing it to be restricted thereby.

EXAMPLES

The following syntheses are carried out under a protective-gas atmosphere, unless indicated otherwise. The starting materials can be purchased from ALDRICH or ABCR (n-butyllithium, 2.5M in hexane, silanes, bromides, inorganics, solvents). 2,6-Dibromoanthraquinone is prepared as described by Lee et al., Org. Lett. 2005, 7(2), 323.

Example 1

2,6-Bis(trimethylsilyl)-9,10-bis(o-tolyl)anthracene a) 2,6-Dibromo-9,10-bis(o-tolyl)anthracene

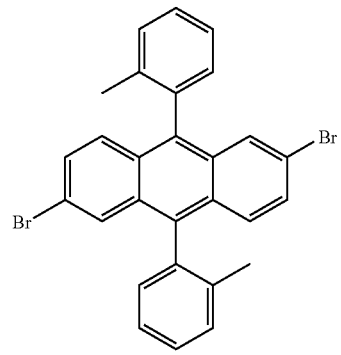 [SMILES: Cc1ccccc1-c1c2ccc(Br)cc2c(-c2ccccc2C)c2ccc(Br)cc12]

The corresponding organolithium reagent is prepared from 18.0 ml (150 mmol) of 2-bromotoluene in 500 ml of THF by addition of 60 ml of n-butyllithium (2.5M in hexane) at −78° C. and stirring for a further 1 h. 27.5 g (75 mmol) of 2,6-dibromoanthraquinone are added to this reagent. The reaction mixture is subsequently stirred at −78° C. for 1 h and warmed to room temperature over the course of 5 h, and a mixture of 100 ml of acetic acid and 200 ml of water is then added. The solid is filtered off with suction, washed with 200 ml of water, 100 ml of ethanol and twice with 200 ml of heptane each time and dried. The solid is refluxed for 3 h with 15.2 g (80 mmol) of tin(II) chloride (anhydrous) in 300 ml of DMF. After cooling, 500 ml of 2.5N hydrochloric acid are added, and the solid is filtered off with suction. The solid is washed three times with 100 ml of 2.5N hydrochloric acid each time, three times with 100 ml of water each time and three times with 100 ml of ethanol each time, dried under reduced pressure and recrystallised twice from DMF. Yield: 33.0 g (64 mmol), 85.2% of theory; purity: 99% according to HPLC.

b) 2,6-Bis(trimethylsilyl)-9,10 bis(o-tolyl)anthracene

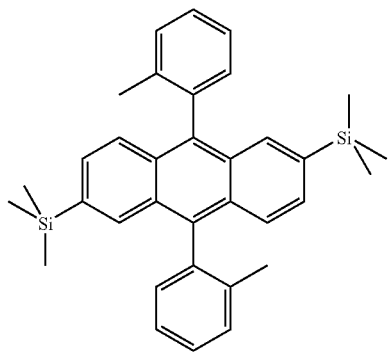

The corresponding organolithium reagent is prepared from 33.0 g (64 mmol) of 2,6-dibromo-9,10-di-o-tolylanthracene in 500 ml of THF by addition of 77 ml of n-butyllithium (2.5M in hexane) at −78° C. and stirring for a further 3 h, and 26.8 ml (210 mmol) of chlorotrimethylsilane are subsequently added. After the mixture has been stirred for a further 1 h and warmed to room temperature, the THF is removed under reduced pressure, the residue is taken up in 500 ml of dichloromethane, and the organic phase is washed three times with 500 ml of water each time, dried, filtered through Celite and freed from solvent under reduced pressure. The residue is recrystallised five times from toluene/acetonitrile and then sub-limed in a high vacuum, $p=1\times10^{-5}$ mbar, T=310° C. Yield: 23.6 g (47 mmol), 73.4% of theory; purity: 99.8% according to HPLC. Mixture of two atropisomers according to $^1$H-NMR spectroscopy.

Example 2

Synthesis of Further Compounds According to the Invention

The following compounds are prepared analogously to Example 1:

| Ex. | Bromide/step a) | Silane/step b) | Product |
|---|---|---|---|
| 3 | | | |
| 4 | | | |

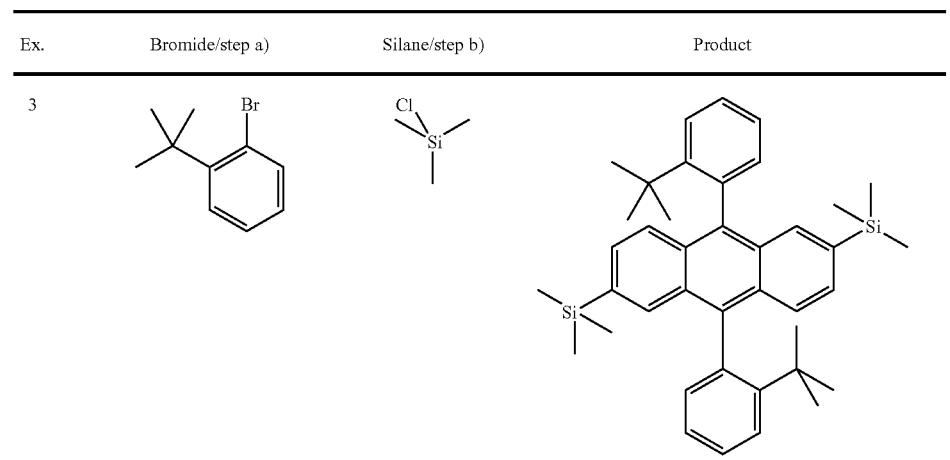

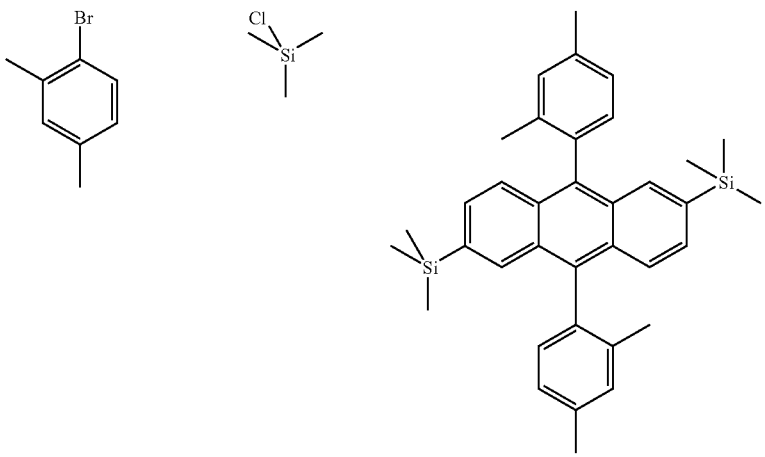

-continued
| Ex. | Bromide/step a) | Silane/step b) | Product |
|---|---|---|---|
| 5 | 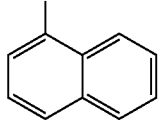 |  | 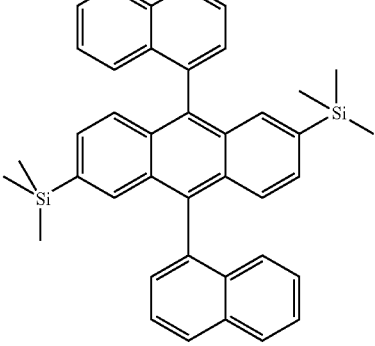 |
| 6 | 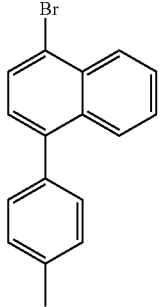 [SMILES: Cc1ccc(-c2ccc(Br)c3ccccc23)cc1] |  | 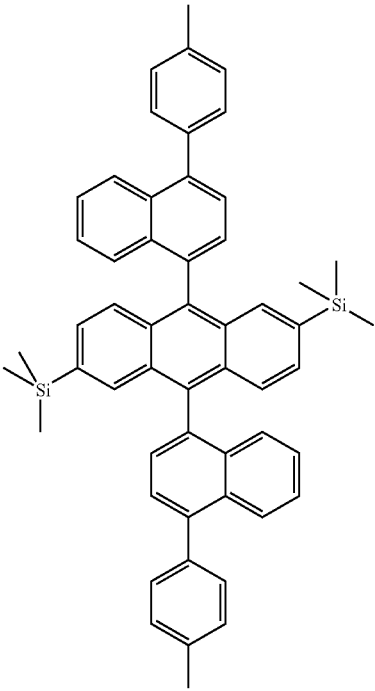 |
| 7 | 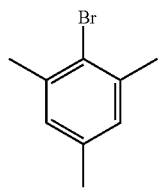 | 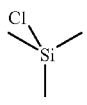 | 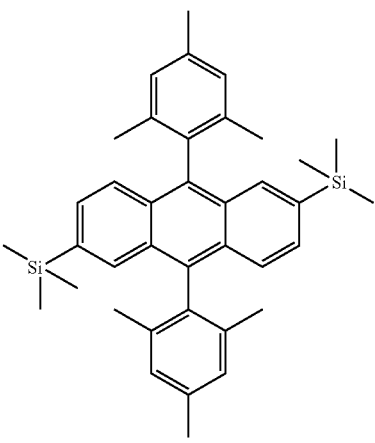 |

-continued
| Ex. | Bromide/step a) | Silane/step b) | Product |
|---|---|---|---|
| 8 | 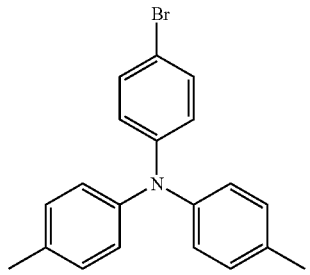 |  | 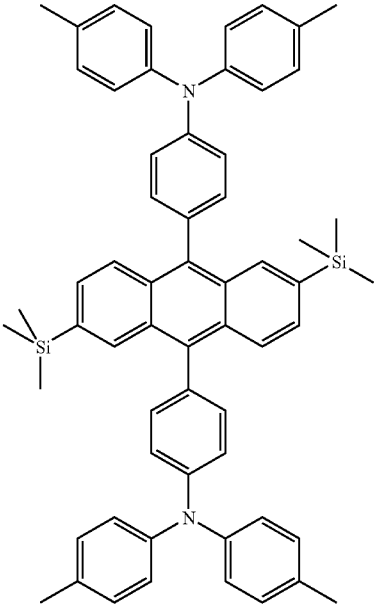 |
| 9 | 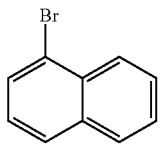 | 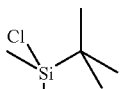 | 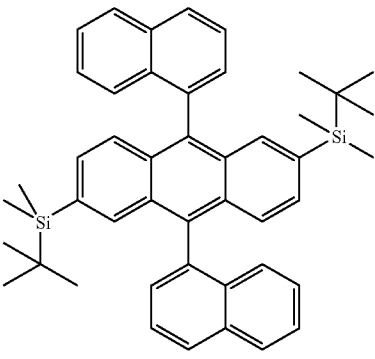 [SMILES: CC(C)(C)[Si](C)(C)c1ccc2c(-c3cccc4ccccc34)c3cc([Si](C)(C)C(C)(C)C)ccc3c(-c3cccc4ccccc34)c2c1] |
| 10 | 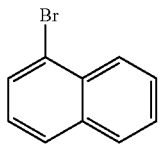 | 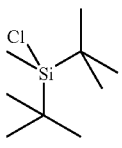 | 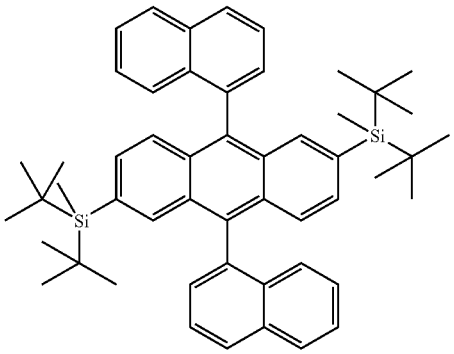 [SMILES: CC(C)(C)[Si](C)(c1ccc2c(-c3cccc4ccccc34)c3cc([Si](C)(C(C)(C)C)C(C)(C)C)ccc3c(-c3cccc4ccccc34)c2c1)C(C)(C)C] |

| Ex. | Bromide/step a) | Silane/step b) | Product |
|---|---|---|---|
| 11 | | | 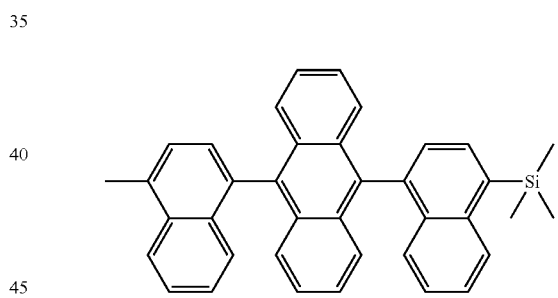 |

Example 12

9-(4-Methylnaphth-1-yl)-10-(4-trimethylsilylnaphthyl)-anthracene a) Synthesis of (4-bromonaphth-1-yl)trimethylsilane

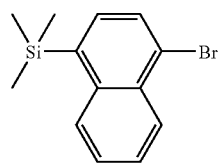

A solution of 114.38 g (400 mmol) of 1,4-dibromonaphthalene and 1 l of THF (absolute) is cooled to −78° C. under protective gas, 160 ml (400 mmol) of n-butyllithium (2.5M in n-hexane) are subsequently slowly added at this temperature, and the mixture is stirred at −78° C. for a further 30 h. A mixture of 52.3 ml (400 mmol) of chlorotrimethylsilane in 200 ml of THF (absolute) is added to the solution obtained in this way, and the mixture is slowly warmed to room temperature. After addition of 150 ml of EtOH and subsequently 300 ml of water, the organic phase is separated off, dried over magnesium sulfate and evaporated. The oil obtained in this way is distilled at 115-135° C. and 1.7 mbar, giving 80 g (286 mmol) (corresponding to 88% of theory) of the product having a purity of greater than 99.0% according to HPLC.

b) Synthesis of 4-(trimethylsiyl)naphth-1-ylboronic acid

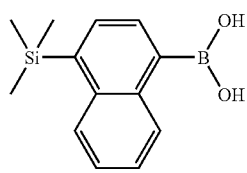 [SMILES: C[Si](C)(C)c1ccc(B(O)O)c2ccccc12]

73.7 ml (184 mmol) of n-butyllithium (2.5M in hexane) are added dropwise to a solution, cooled to −78° C., of 46.8 g (167.6 mmol) of (4-bromonaphth-1-yl)trimethylsilane in 950 ml of diethyl ether. The reaction mixture is stirred at −78° C. for 30 min., warmed to room temperature, then re-cooled to −78° C., and a mixture of 26.4 ml (234 mmol) of trimethyl borate in 50 ml of diethyl ether is added rapidly. After warming to −10° C., the mixture is hydrolysed using 90 ml of 2N hydrochloric acid. The organic phase is separated off, washed with water, dried over sodium sulfate and evaporated to dryness. The residue is taken up in 200 ml of n-heptane, and the colourless solid is filtered off with suction, washed with n-heptane and dried under reduced pressure. Yield: 26 g (106 mmol), 45% of theory; purity; 98% according to $^1$H-NMR.

c) Synthesis of 9-(4-methylnaphth-1-yl)-10-(4-trimethylsilyinaphthyl)anthracene 1.78 g (5.6 mmol) of tri-o-tolylphosphine and 0.2 g (0.9 mmol) of palladium acetate are added to a vigorously stirred, degassed suspension of 22.8 g (93.3 mmol) of 4-trimethylsilyinaphth-1-ylboronic acid, 37.4 g (93.3 mmol) of 9-(4-methylnaphth-1-yl)anthracene and 90 g (230 mmol) of tripotassium phosphate in a mixture of 575 ml of water, 100 ml of dioxane and 860 ml of toluene, and the mixture is refluxed for 60 h. After cooling, the organic phase is separated off, washed three times with 200 ml of water and once with 200 ml of saturated aqueous sodium chloride solution and subsequently dried over magnesium sulfate. After the desiccant has been filtered off, the organic phase is evaporated to dryness under reduced pressure in a rotary evaporator. The grey residue obtained in this way is recrystallised from dioxane. The deposited crystals are filtered off with suction, washed with 50 ml of ethanol and subsequently dried under reduced pressure; yield: 38 g, 79% of theory; purity: 99.9% according to HPLC.

Example 13

9,10-Bis(4-trimethylsitylnaphthyl)anthracene

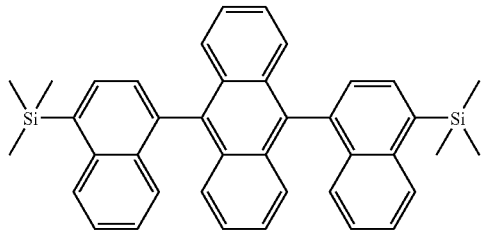

2.6 g (9.7 mmol) of tri-o-tolylphosphine and 0.365 g (1.63 mmol) of palladium acetate are added to a vigorously stirred, degassed suspension of 29.7 g (122 mmol) of 4-trimethylsilylinaphth-1-ylboronic acid (from Example 12b), 13.6 g (40.6 mmol) of 9,10-dibromoanthracene and 41 g (178 mmol) of tripotassium phosphate in a mixture of 163 ml of water, 200 ml of dioxane and 200 ml of toluene, and the mixture is refluxed for 60 h. After cooling, the organic phase is separated off, washed three times with 200 ml of water and once with 200 ml of saturated aqueous sodium chloride solution and subsequently dried over magnesium sulfate. After the desiccant has been filtered off, the organic phase is evaporated to dryness under reduced pressure in a rotary evaporator. The grey residue obtained in this way is recrystallised from dioxane. The deposited crystals are filtered off with suction, washed with 50 ml of ethanol and subsequently dried under reduced pressure; yield: 23 g, 78% of theory; purity: 99.9% according to HPLC.

Example 14

Production of OLEDs

OLEDs are produced by a general process as described in WO 04/058911, which is adapted in the individual case to the respective circumstances (for example layer-thickness variation in order to achieve optimum efficiency or colour). The basic structure and the materials used (apart from the emitting layer) are identical in the examples for better comparability. OLEDs having the following structure are produced analogously to the above-mentioned general process:

| | |
|---|---|
| Hole-transport layer (HTL) | 20 nm 2,2',7,7'-tetrakis(di-para-tolylamino)-spiro-9,9'-bifluorene (abbreviated to HTL-1) |
| Hole-transport layer (HTL) | 20 nm NPB (N-naphthyl-N-phenyl-4,4'-diaminobiphenyl) |
| Emission layer (EML) | see Table 1 for materials, concentration and layer thickness |
| Electron conductor (ETL) | 20 nm AlQ$_3$ (purchased from SynTec, tris(quinolinato)aluminium(III)) |
| Cathode | 1 nm LiF, 150 nm Al on top. |

These OLEDs are characterised by standard methods; for this purpose, the electroluminescence spectral the efficiency (measured in cd/A), the power efficiency (measured in lm/W) as a function of the brightness, calculated from current/voltage/brightness characteristic lines (IUL characteristic lines), and the lifetime are determined. The lifetime is defined as the time after which the initial brightness of 1000 cd/m$^2$ has dropped to half.

Table 2 shows the results for some OLEDs (Examples 2 to 9) which comprise dopants D1, D2 and the compound from Example 8, where in each case the composition of the EML including the layer thicknesses is also given.

The structure of the dopants is depicted below:

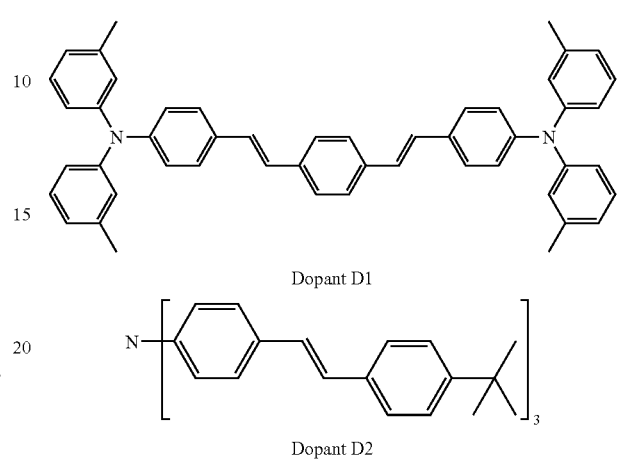

Dopant D1

Dopant D2

The compounds from Examples 5, 10, 12 and 13 are employed as host material according to the invention. For comparison, host materials H1 and H2 are employed as host material in accordance with the prior art. The host materials are depicted below:

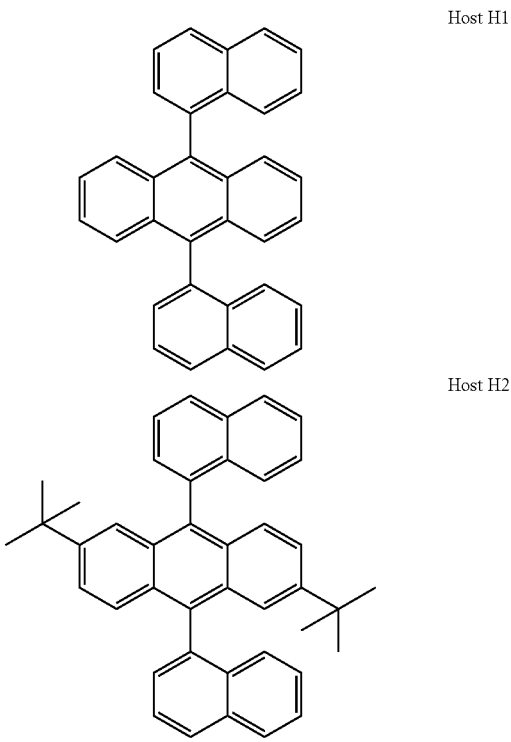

Host H1

Host H2

As can be seen from the examples in Table 2, the electroluminescent devices according to the invention exhibit higher efficiency and a longer lifetime with comparable colour coordinates compared with electroluminescent devices in accordance with the prior art.

TABLE 2

| Example | EML | Max. efficiency (cd/A) | Voltage (V) at 100 cd/m² | CIE | Lifetime (h) |
|---|---|---|---|---|---|
| Example 15 (comparison) | H1: D1 (3%) (30 nm) | 11.8 | 5.5 | x = 0.17; y = 0.32 | 6700 |
| Example 16 (comparison) | H1: D1 (5%) (30 nm) | 12.2 | 5.3 | x = 0.17; y = 0.33 | 7000 |
| xample 17 (comparison) | H1: D1 (7%) (30 nm) | 11.5 | 5.2 | x = 0.18; y = 0.36 | 5300 |
| Example 18 (comparison) | H2: D1 (5%) (30 nm) | 11.8 | 5.0 | x = 0.17; y = 0.35 | 7800 |
| Example 19 | Example 13: D1 (3%) (30 nm) | 11.0 | 5.4 | x = 0.17; y = 0.33 | 7200 |
| Example 20 | Example 13: D1 (5%) (30 nm) | 12.4 | 5.2 | x = 0.17; y = 0.35 | 7900 |
| Example 21 | Example 12: D1 (3%) (30 nm) | 11.8 | 5.3 | x = 0.17; y = 0.32 | 8000 |
| Example 22 | Example 12: D1 (5%) (30 nm) | 12.8 | 5.1 | x = 0.17; y = 0.32 | 8500 |
| Example 23 | Example 10: D1 (5%) (30 nm) | 13 | 4.8 | x = 0.18; y = 0.37 | 8800 |
| Example 24 | Example 5: D1 (5%) (30 nm) | 12.8 | 5.0 | x = 0.17; y = 0.35 | 8400 |
| Example 25 (comparison) | H1: D2 (5%) (30 nm) | 4.2 | 5.1 | x = 0.15; y = 0.11 | 1600 |
| Example 26 | Example 10: D2 (5%) (30 nm) | 5.1 | 5.1 | x = 0.15; y = 0.14 | 2200 |
| Example 27 | Example 12: D2 (5%) (30 nm) | 4.5 | 5.0 | x = 0.15; y = 0.12 | 3000 |
| Example 28 | H1: Example 8 (5%) (30 nm) | 6.1 | 5.1 | x = 0.15; y = 0.17 | 4000 |
| Example 29 | Example 12: Example 8 (5%) (30 nm) | 6.2 | 4.8 | x = 0.15; y = 0.16 | 4500 |

The invention claimed is:

1. An organic electronic device comprising at least one silyl-substituted compound represented by formula (1)

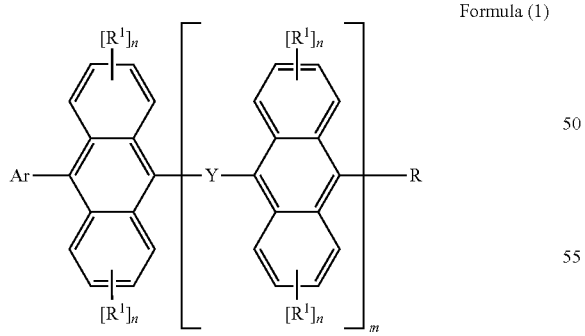

Formula (1)

wherein

Ar is a 1-naphthyl group or a 9-anthryl group, each optionally substituted by one or more radicals R1 and/or one or more radicals $N(Ar^1)_2$, wherein one or two carbon atoms of said 1-naphthyl group or said 9-anthryl group is optionally replaced by N, and wherein the two radicals $Ar^1$ are optionally connected to one another by a single bond or an O, S, $N(R^1)$, or $C(R^1)_2$ group;

R is an aromatic or heteroaromatic ring system having 5 to 40 aromatic ring atom sand optionally substituted by one or more radicals $R^1$ or an $N(Ar^1)_2$ group, where the two radicals $Ar^1$ are optionally connected to one another by a single bond or an O, S, $N(R^1)$, or $C(R^1)_2$ group;

$Ar^1$ is, identically or differently on each occurrence, an aromatic or heteroaromatic ring system having 5 to 40 aromatic ring atoms and optionally substituted by one or more radicals $R^1$;

Y is, identically or differently on each occurrence, a divalent group containing up to 40 C atoms, —O—, —S—, —$NR^1$—, —$P(=O)R^1$—, or a single bond;

$R^1$ is, identically or differently on each occurrence, $Si(R^2)_3$; F; Cl; Br; I; CN; $N(R^3)_2$; $NO_2$; a straight-chain alkyl, alkoxy or thioalkoxy group having 1 to 40 C atoms and optionally substituted by one or more radicals $R^3$, wherein one or more non\-adjacent $CH_2$ groups are optionally replaced by —$R_3C=CR_3$—, —C≡C—, $Si(R^3)_2$, $Ge(R^3)_2$, $Sn(R^3)_2$, C=O, C=S, C=Se, C=$NR^3$, —O—, —S—, —$N(R^3)$—, or —$CONR^3$— and wherein one or more H atoms are optionally replaced by F, Cl, Br, I, CN, or $NO_2$; a branched or cyclic alkyl, alkoxy or thioalkoxy group having 3 to 40 C atoms and optionally substituted by one or more radicals $R^3$, wherein one or more non-adjacent $CH_2$ groups are optionally replaced by —$R_3C=CR_3$—, —C≡C—, $Si(R^3)_2$, $Ge(R^3)_2$, $Sn(R^3)_2$, C=O, C=S, C=Se, C=$NR_3$, —O—, —S—, —N($R_3$)—, or —$CONR_3$— and wherein one or more H atoms are optionally replaced by F, Cl, Br, I, CN, or $NO_2$; an aryl or heteroaryl group having 5 to 24 aromatic ring atoms and optionally substituted by one or more radicals $R_3$; or an aryloxy or heteroaryloxy group having 5 to 24 aromatic ring atoms and optionally substituted by one or more radicals $R_3$; or a combination of two, three, four or five of these systems; and wherein two or more adjacent substituents $R^1$ optionally define a mono- or polycyclic, aliphatic ring system with one another;

$R^2$ is, identically or differently on each occurrence, a straight-chain alkyl group having up to 40 C atoms and optionally substituted by an aryl or heteroaryl group having 5 to 24 aromatic ring atoms optionally substituted by one or more radicals $R^3$ or an aryloxy or heteroaryloxy group having 5 to 24 aromatic ring atoms optionally substituted by one or more radicals $R^3$; wherein one or more non-adjacent $CH_2$ groups which are not bonded directly to silicon are optionally replaced by —$R_3C=CR_3$—, —C≡C—, $Si(R^3)_2$, $Ge(R^3)_2$, $Sn(R^3)_2$, C=O, C=S, C=Se, C=$NR^3$, —O—, —S—, —N($R^3$)—, or —$CONR^3$—, and wherein one or more H atoms is optionally replaced by F, Cl, Br, I, CN, or $NO_2$; a branched or cyclic alkyl group having 3 to 40 C atoms optionally substituted by an aryl or heteroaryl group having 5 to 24 aromatic ring atoms optionally substituted by one or more radicals $R^3$ or an aryloxy or heteroaryloxy group having 5 to 24 aromatic ring atoms optionally substituted by one or more radicals $R^3$, wherein one or more non-adjacent $CH_2$ groups which are not bonded directly to silicon are optionally replaced by —$R^3C=CR^3$—, —C≡C—, $Si(R^3)_2Ge(R^3)_2$, $(R^3)_2$, C=O, C=S, C=Se, C=$NR^3$, —O—, —S—, —N($R^3$)—, or —$CONR^3$—, and wherein one or more H atoms is optionally replaced by F, Cl, Br, I, CN, or $NO_2$; and wherein two or more substituents $R^2$ optionally define a mono- or polycyclic ring system with one another;

$R^3$ is, identically or differently on each occurrence, H or a hydrocarbon radical having up to 20 C atoms, which may be aliphatic or aromatic or a combination of aliphatic and aromatic and is optionally substituted by F; and wherein two or more radicals $R^3$ optionally define a mono- or polycyclic, aliphatic or aromatic ring system with one another;

n is, identically or differently on each occurrence, 0, 1, 2, 3, or 4; and m is 0, 1, 2, 3, 4, or 5;

with the proviso that at least one radical $R^1$ which is an $Si(R^2)_3$ group is present and is bonded to the central anthracene unit in the 2-position and/or in the 6-position, and/or, when Ar is 1-naphthyl, is bonded to the 1-naphthyl group in the 4-position and, when Ar is 9-anthyl, is bonded to the 9-anthryl group in the 10-position, and/or is bonded to the R group.

2. The organic electronic device of claim 1, wherein the silyl-substituted compound is represented by formula (1a), (1b), (1c), or (1d):

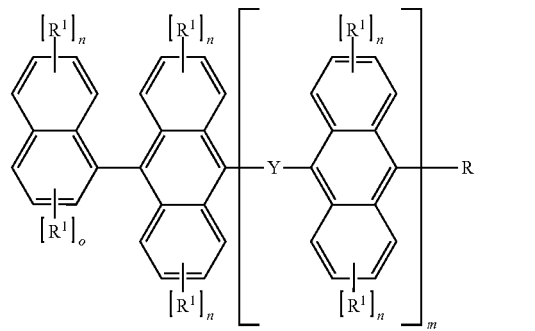

Formula (1a)

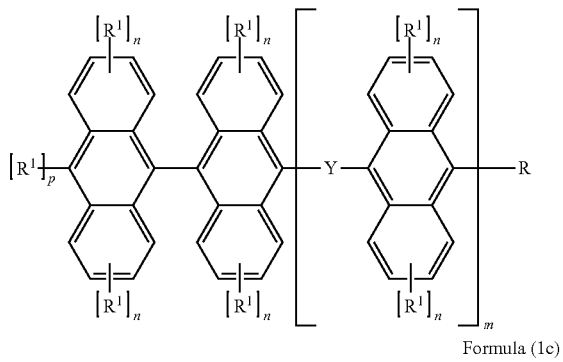

Formula (1b)

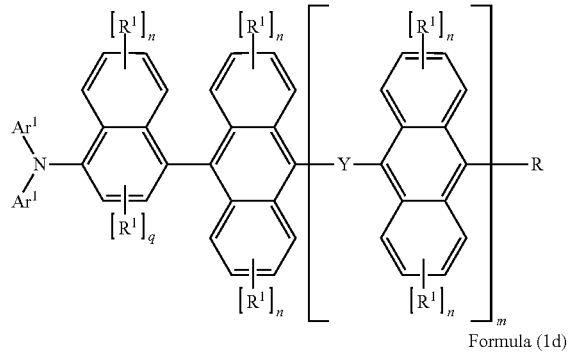

Formula (1c)

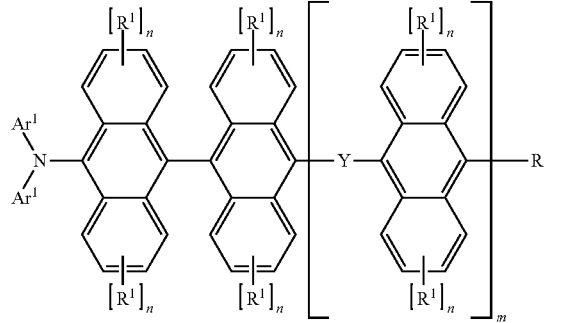

Formula (1d)

wherein the two radicals $Ar^1$ are optionally connected to one another by a single bond or an O, S, N($R^1$), or C($R^1$)$_2$ group;

o is 0, 1, 2, or 3;

p is 0 or 1; and q is 0, 1 or 2.

3. The organic electronic device of claim 2 comprising the silyl-substituted compound wherein p is 1.

4. The organic electronic device of claim 1 comprising the silyl-substituted compound, wherein R is an aromatic or heteroaromatic ring system having 6 to 24 aromatic ring atoms and optionally substituted by one or more radicals $R^1$; or is a group of formula (2a) or (2b)

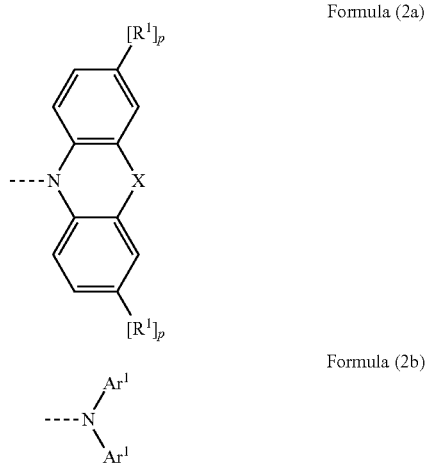

Formula (2a)

Formula (2b)

wherein
X is a single bond, O, S, $N(R^1)$, or $C(R^1)_2$;
$Ar^1$ is, identically or differently on each occurrence, an aryl or heteroaryl group having 5 to 20 aromatic ring atoms and optionally substituted by one or more radicals $R^1$.

5. The organic electronic device of claim 4 comprising the silyl-substituted compound, wherein said aryl or heteroaryl group has 6 to 14 aromatic ring atoms and is optionally substituted by one or more radicals $R^1$.

6. The organic electronic device of claim 5 comprising the silyl-substituted compound, wherein said aryl or heteroaryl group is phenyl, 1-naphthyl, or 2-naphthyl, each of which is optionally substituted by one or more radicals R1.

7. The organic electronic device of claim 1 comprising the silyl-substituted compound, wherein R is a condensed aryl or heteroaryl group having 10 to 16 aromatic ring atoms or an aromatic, optionally bridged biaryl group, each of which is optionally substituted by one or more radicals $R^1$.

8. The organic electronic device of claim 7 comprising the silyl-substituted compound wherein R is a 1-naphthyl, 2-naphthyl, 9-anthryl, 2-phenanthrenyl, 9-phenanthrenyl, quinolinyl, isoquinolinyl, ortho-biphenyl, meta-biphenyl, para-biphenyl, 2-fluorenyl, or 2-spirobifluorenyl group, each of which is optionally substituted by one or more radicals $R^1$.

9. The organic electronic device of claim 1 comprising the silyl-substituted compound wherein R1 is, identically or differently on each occurrence, $Si(R^2)_3$; F; a straight-chain alkyl or alkoxy group having up to 6 C atoms wherein one or more $CH_2$ groups is optionally replaced by —$R^3C$=C $R^3$—, $Si(R^3)_2$, —O—, —S—, or —$N(R^3)$— and wherein one or more H atoms is optionally replaced by F; a branched or cyclic alkyl or alkoxy group having 3 to 10 C atoms, wherein one or more CH2 groups is optionally replaced by —$R^3C$=C $R^3$—, $Si(R^3)_2$, —O—, —S—, or —$N(R^3)$— and wherein one or more H atoms is optionally replaced by F; or an aryl or heteroaryl group having 5 to 14 aromatic ring atoms and optionally substituted by one or more radicals $R^3$; or a combination of two or three of these systems; and wherein two or more radicals $R^1$ optionally define a mono- or polycyclic, aliphatic ring system with one another.

10. The organic electronic device of claim 1 comprising the silyl-substituted compound wherein Y is, identically or differently on each occurrence, a linear alkylene group having up to 10 C atoms, a branched or cyclic alkylene or alkylidene group having 3 to 10 C atoms, a divalent aromatic group having 6 to 25 C atoms, C=O, —O—, —S—, —$N(R^1)$—, —$P(=O)R^1$—, or a single bond.

11. The organic electronic device of claim 1 comprising the silyl-substituted compound wherein it contains one, two, three, or four groups of formula $Si(R^2)_3$.

12. The organic electronic device of claim 1 comprising the silyl-substituted compound wherein $R^2$ of $Si(R^2)_3$ is selected from the group consisting of straight-chain alkyl groups having up to 10 C atoms, wherein one or more non-adjacent CH2 groups which are not bonded directly to the silicon are optionally replaced by O and wherein one or more H atoms is optionally replaced by F, and branched or cyclic alkyl groups having 3 to 10 C atoms, wherein one or more non-adjacent $CH_2$ groups which are not bonded directly to the silicon are optionally replaced by O and wherein one or more H atoms is optionally replaced by F; and wherein two or more substituents $R^2$ optionally define a mono- or polycyclic ring system with one another.

13. The organic electronic device of claim 1, wherein said device is selected from the group consisting of organic electroluminescent devices, organic field-effect transistors, organic thin-film transistors, organic light-emitting transistors, organic integrated circuits, organic solar cells, organic field-quench devices, organic photoreceptors, light-emitting electrochemical cells, and organic laser diodes.

14. The organic electronic device of claim 1, wherein said device is an organic electroluminescent device comprising at least one emitting layer, hole-transport layer, hole-injection layer, hole-blocking layer, and/or electron-transport layer, wherein at least one of said layers comprises at least one silyl-substituted compound of formula (1)

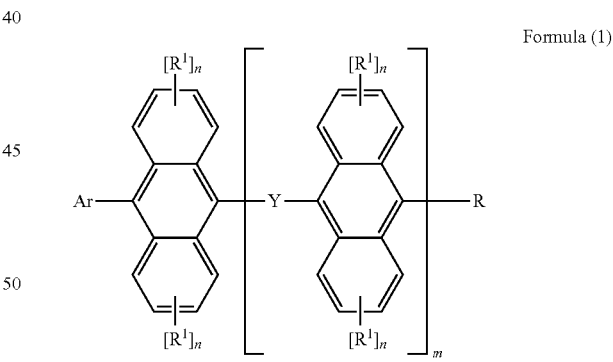

Formula (1)

wherein
Ar is a 1-naphthyl group or a 9-anthryl group, each optionally substituted by one or more radicals $R^1$ and/or one or more radicals $N(Ar^1)_2$, wherein one or two carbon atoms of said 1-naphthyl group or said 9-anthryl group is optionally replaced by N, and wherein the two radicals $Ar^1$ are optionally connected to one another by a single bond or an O, S, $N(R^1)$, or $C(R^1)_2$ group;
R is an aromatic or heteroaromatic ring system having 5 to 40 aromatic ring atoms and optionally substituted by one or more radicals $R^1$ or an $N(Ar^1)_2$ group, where the two radicals $Ar^1$ are optionally connected to one another by a single bond or an O, S, $N(R^1)$, or $C(R^1)_2$ group;

Ar$^1$ is, identically or differently on each occurrence, an aromatic or heteroaromatic ring system having 5 to 40 aromatic ring atoms and optionally substituted by one or more radicals R$^1$;

Y is, identically or differently on each occurrence, a divalent group containing up to 40 C atoms, —O—, —S—, —NR$^1$—, —P(=O)R1-, or a single bond;

R$^1$ is, identically or differently on each occurrence, Si(R$^2$)$_3$; F; Cl; Br; I; CN; N(R$^2$)$_3$; NO$_2$; a straight-chain alkyl, alkoxy or thioalkoxy group having 1 to 40 C atoms and optionally substituted by one or more radicals R$^3$, wherein one or more non-adjacent CH$_2$ groups are optionally replaced by —R$^3$C=CR$^3$—, —C≡C—, Si(R$^3$)$_2$, Ge(R$^2$)$_3$, Sn(R$^2$)$_3$, C=O, C=S, C=Se, C=NR$^3$, —O—, —S—, —N(R$^3$)—, or —CONR$^3$— and wherein one or more H atoms are optionally replaced by F, Cl, Br, I, CN, or NO$_2$; a branched or cyclic alkyl, alkoxy or thioalkoxy group having 3 to 40 C atoms and optionally substituted by one or more radicals R$^3$, wherein one or more non-adjacent CH$_2$ groups are optionally replaced by —R$^3$C=CR$^3$—, —C≡C—, Si(R$^2$)$_3$, Ge(R$^2$)$_3$, Sn(R$^2$)$_3$, C=O, C=S, C=Se, C=NR$^3$, —O—, —S—, —N(R$^3$)—, or —CONR$^3$— and wherein one or more H atoms are optionally replaced by F, Cl, Br, I, CN, or NO2; an aryl or heteroaryl group having 5 to 24 aromatic ring atoms and optionally substituted by one or more radicals R$^3$; or an aryloxy or heteroaryloxy group having 5 to 24 aromatic ring atoms and optionally substituted by one or more radicals R$^3$; or a combination of two, three, four or five of these systems; and wherein two or more adjacent substituents R$^1$ optionally define a mono- or polycyclic, aliphatic ring system with one another;

R$^2$ is, identically or differently on each occurrence, a straight-chain alkyl group having up to 40 C atoms and optionally substituted by an aryl or heteroaryl group having 5 to 24 aromatic ring atoms optionally substituted by one or more radicals R$^3$ or an aryloxy or heteroaryloxy group having 5 to 24 aromatic ring atoms optionally substituted by one or more radicals R3; wherein one or more non-adjacent CH$_2$ groups which are not bonded directly to silicon are optionally replaced by —R$^3$C=CR$^3$—, —C≡C—, Si(R$^2$)$_3$, Ge(R$^2$)$_3$, Sn(R$^2$)$_3$, C=O, C=S, C=Se, C=NR$^3$, —O—, —S—, —N(R$^3$)—, or —CONR$^3$—, and wherein one or more H atoms is optionally replaced by F, Cl, Br, I, CN, or NO$_2$; a branched or cyclic alkyl group having 3 to 40 C atoms optionally substituted by an aryl or heteroaryl group having 5 to 24 aromatic ring atoms optionally substituted by one or more radicals R$^3$ or an aryloxy or heteroaryloxy group having 5 to 24 aromatic ring atoms optionally substituted by one or more radicals R$^3$, wherein one or more non-adjacent CH$_2$ groups which are not bonded directly to silicon are optionally adjacent CH$_2$ groups are optionally replaced by —R$^3$C=CR$^3$—, —C≡C—, Si(R$^2$)$_3$, Ge(R$^2$)$_3$, Sn(R$^2$)$_3$, C=O, C=S, C=Se, C=NR$^3$, —O—, —S—, —N(R$^3$)—, or —CONR$^3$— and wherein one or more H atoms are optionally replaced by F, Cl, Br, I, CN, or NO$_2$; a branched or cyclic alkyl, alkoxy or thioalkoxy group having 3 to 40 C atoms and optionally substituted by one or more radicals R$^3$, wherein one or more non-adjacent CH$_2$ groups are optionally replaced by —R$^3$C=CR$^3$— C≡C—, Si(R$^2$)$_3$, Ge(R$^2$)$_3$, Sn(R$^2$)$_3$, C=O, C=S, C=Se, C=NR$^3$, —O—, —S—, —N(R$^3$)—, or —CONR$^3$— and wherein one or more H atoms are optionally replaced by F, Cl, Br, I, CN, or NO$_2$; an aryl or heteroaryl group having 5 to 24 aromatic ring atoms and optionally substituted by one or more radicals R$^3$; or an aryloxy or heteroaryloxy group having 5 to 24 aromatic ring atoms and optionally substituted by one or more radicals R$^3$; or a combination of two, three, four or five of these systems; and wherein two or more adjacent substituents R$^1$ optionally define a mono- or polycyclic, aliphatic ring system with one another;

R$^3$ is, identically or differently on each occurrence, H or a hydrocarbon radical having up to 20 C atoms, which may be aliphatic or aromatic or a combination of aliphatic and aromatic and is optionally substituted by F; and wherein two or more radicals R$^3$ optionally define a mono- or polycyclic, aliphatic or aromatic ring system with one another;

n is, identically or differently on each occurrence, 0, 1, 2, 3, or 4; and m is 0, 1, 2, 3, 4, or 5;

wherein at least one radical R$^1$ which represents a Si(R$^2$)$_3$ group is present.

15. The organic electronic device of claim 14, wherein said at least one silyl-substituted compound of formula (1) is employed as host material for fluorescent emitters and/or as electron-transport material and/or as hole-blocking material when R is an aromatic or heteroaromatic ring system.

16. The organic electronic device of claim 14, wherein said at least one silyl-substituted compound of formula (1) is employed as emitting compound and/or as hole-transport material when R is N(Ar$^1$)$_2$.

17. The organic electronic device of claim 1 comprising the silyl-substituted compound wherein R$^2$ is a straight-chain alkyl group having 1 to 4 C atoms or a branched alkyl group having 3 or 4 C atoms, wherein said straight-chain and branched alkyl groups are optionally substituted with fluorine atoms.

18. The organic electronic device of claim 1 comprising the silyl-substituted compound wherein R$^2$ is selected from the group consisting of methyl, CF$_3$, ethyl, isopropyl, and tert-butyl.

19. The organic electronic device of claim 1 comprising the silyl-substituted compound wherein Si(R$^2$)$_3$ is selected from the group consisting of Si(Me)$_3$, Si(Me)$_2$(t-Bu), SiMe(t-Bu)$_2$, and Si(i-Pr)$_3$.

20. The organic electronic device of claim 1 comprising the silyl-substituted compound, wherein Ar and R are identical.

* * * * *